(12) United States Patent
Hibbs et al.

(10) Patent No.: US 9,457,374 B2
(45) Date of Patent: Oct. 4, 2016

(54) METHOD AND APPARATUS FOR CURTAIN COATING

(71) Applicant: UPM RAFLATAC OY, Tampere (FI)

(72) Inventors: David Hibbs, Fletcher, NC (US); Anthony Blackman, Pisgah Forest, NC (US)

(73) Assignee: UPM RAFLATAC OY, Tampere (FI)

( * ) Notice: Subject to any disclaimer, the term of this patent is extended or adjusted under 35 U.S.C. 154(b) by 154 days.

(21) Appl. No.: 14/075,806

(22) Filed: Nov. 8, 2013

(65) Prior Publication Data

US 2015/0132471 A1    May 14, 2015

(51) Int. Cl.
| | | |
|---|---|---|
| *B05D 1/30* | (2006.01) | |
| *B05C 5/00* | (2006.01) | |
| *G06T 7/00* | (2006.01) | |
| *B05C 11/10* | (2006.01) | |
| *G01B 11/25* | (2006.01) | |
| *G01B 11/00* | (2006.01) | |
| *G01N 21/85* | (2006.01) | |

(52) U.S. Cl.
CPC ............... *B05D 1/305* (2013.01); *B05C 5/005* (2013.01); *B05C 11/1007* (2013.01); *G06T 7/001* (2013.01); *G01B 11/00* (2013.01); *G01B 11/254* (2013.01); *G01N 2021/8557* (2013.01); *G06T 2207/30124* (2013.01)

(58) Field of Classification Search
CPC ........................ G01N 2021/8557; B05D 1/305
See application file for complete search history.

(56) References Cited

U.S. PATENT DOCUMENTS

| | | | | |
|---|---|---|---|---|
| 5,190,789 | A * | 3/1993 | Finnicum | ............... B05C 5/008 118/324 |
| 2001/0041213 | A1* | 11/2001 | Emonot | ................. B05C 5/005 427/8 |
| 2003/0067538 | A1* | 4/2003 | Myers | ............... G01B 11/2509 348/47 |
| 2008/0311299 | A1* | 12/2008 | Furukawa | ................. B41J 3/44 427/261 |
| 2010/0077849 | A1* | 4/2010 | Jakimov | ............... G01B 21/08 73/150 R |

* cited by examiner

*Primary Examiner* — Michael P Rodriguez
(74) *Attorney, Agent, or Firm* — Venable LLP; Eric J. Franklin

(57) ABSTRACT

A curtain coating method including forming a curtain including a coating material. A coated web is formed by coating a moving primary web with the coating material. The curtain and the primary web meet at a contact line. A primary pattern is projected on a material layer. The material layer moves with respect to the contact line. The primary pattern includes a first pointer feature. A first image is captured. The first image includes a first sub-image of the first pointer feature. The position of the first sub-image in the first image is detected. Distance information is provided by comparing the detected position of the first sub-image with a reference position.

14 Claims, 22 Drawing Sheets

METHOD AND APPARATUS FOR CURTAIN COATING

FIELD

The present invention relates to curtain coating.

BACKGROUND

A coated web may be produced by a curtain coating method. The curtain coating method may comprise forming a curtain of a fluid, which falls onto a primary web in order to produce a coated web. The curtain may sometimes have a void portion, and the produced web produced by the curtain coating method may need to be rejected due to inferior quality.

SUMMARY

Some variations may relate to a method for curtain coating. Some variations may relate to an apparatus for curtain coating. Some variations may relate to a computer program for monitoring curtain coating. Some variations may relate to a computer program product for monitoring curtain coating. Some variations may relate to a combination of a coated web and auxiliary data.

According to a first aspect, there is provided a method, comprising:
- forming a curtain (CUR1), which comprises a coating material (ADH0),
- forming a coated web (WEB1) by coating a moving primary web (WEB0) with the coating material (ADH0), wherein the curtain (CUR1) and the primary web (WEB1) meet at a contact line (CL1),
- projecting a primary pattern (PTRN1) on a material layer (CUR1, WEB0, WEB1), whose material moves with respect to the contact line (CL1), wherein the primary pattern (PTRN1) comprises a first pointer feature ($D_{A,k}$),
- capturing a first image (FRAME1), which comprises a first sub-image ($SD_{A,k}$) of the first pointer feature ($D_{A,k}$),
- detecting the position ($u_k(t_1)$) of the first sub-image ($SD_{A,k}$) in the first image (FRAME1), and
- providing distance information ($z(t), L_k(t)$) by comparing the detected position ($u_k(t_1)$) of the first sub-image ($SD_{A,k}$) with a reference position ($REF1_k$).

According to a second aspect, there is provided an apparatus (900), comprising:
- one or more rolls (550) arranged to move a primary web (WEB0),
- a distributor unit (510) arranged to form a curtain (CUR1), which comprises a coating material (ADH0), and to form a coated web (WEB1) by coating the primary web (WEB0) with the coating material (ADH0) such that the curtain (CUR1) meets the primary web (WEB0) at a contact line (CL1),
- a projection unit (200) arranged to project a primary pattern (PTRN1) on a material layer (ADH0, WEB0, WEB1), whose material is arranged to move with respect to the contact line (CL1), wherein the primary pattern (PTRN1) comprises a first pointer feature ($D_{A,k}$),
- an imaging unit (100) arranged to capture a first image (FRAME1), which comprises a first sub-image ($SD_{A,k}$) of the first pointer feature ($D_{A,k}$), and
- one or more data processors (CNT1) configured to provide distance information ($z(t), L_k(t)$) by comparing the position ($u_k(t_1)$) of the first sub-image ($SD_{A,k}$) with a reference position ($REF1_k$).

According to a further aspect, there is provided a method, comprising:
- forming a curtain (CUR1), which comprises a coating material (ADH0),
- forming a coated web (WEB1) by coating a moving primary web (WEB0) with the coating material (ADH0),
- projecting a primary pattern (PTRN1) on the curtain (CUR1), wherein the primary pattern (PTRN1) comprises a first pointer feature ($D_{A,k}$),
- capturing a first image (FRAME1), which comprises a first sub-image ($SD_{A,k}$) of the first pointer feature ($D_{A,k}$),
- detecting the position ($u_k(t_1)$) of the first sub-image ($SD_{A,k}$) in the first image (FRAME1), and
- providing distance information ($z(t), L_k(t)$) by comparing the detected position ($u_k(t_1)$) of the first sub-image ($SD_{A,k}$) with a reference position ($REF1_k$).

According to a further aspect, there is provided an apparatus (900), comprising:
- one or more rolls (550) arranged to move a primary web (WEB0),
- a distributor unit (510) arranged to form a curtain (CUR1), which comprises a coating material (ADH0), and to form a coated web (WEB1) by coating the moving primary web (WEB0) with the coating material (ADH0),
- a projection unit (200) arranged to project a primary pattern (PTRN1) on the curtain (CUR1) such that the primary pattern (PTRN1) comprises a first pointer feature ($D_{A,k}$),
- an imaging unit (100) arranged to capture a first image (FRAME1), which comprises a first sub-image ($SD_{A,k}$) of the first pointer feature ($D_{A,k}$), and
- one or more data processors (CNT1) configured to provide distance information ($z(t), L_k(t)$) by comparing the position ($u_k(t_1)$) of the first sub-image ($SD_{A,k}$) with a reference position ($REF1_k$).

According to a further aspect, there is provided a combination of a web (WEB1, WEB3) and data (DATA1), wherein the web (WEB1, WEB3) has been produced by curtain coating, and the data (DATA1) comprises defect data, which indicates the positions ($x'_j, y'_j$) of one or more defect portions ($F_j, F_{j+1}$) of the web (WEB1, WEB3).

A method for curtain coating may comprise forming a curtain, which comprises a coating material. The coating material of the curtain may be substantially in a liquid state. A coated web may be formed by coating a moving primary web with the coating material of the curtain. The coating material of the curtain may fall downwards until it touches the moving primary web. In particular, the coating material may be brought into contact with the primary web at a contact line.

The method may include providing several material layers, which are moving with respect to contact line during the curtain coating. In particular, the primary web, the coated web, and the material of the curtain may move with respect to contact line. The material layers may have deflected portions, deformed portions, and/or void portions, which may have an adverse effect on the quality of the coated web. The material layers may be monitored by determining distance information. The method may comprise projecting one or more pointer features on a material layer, capturing an image, which comprises sub-images of the pointer features, and determining distance information from the positions of the sub-images of the pointer features.

Using the distance information may allow optimization of operating parameters of the coating process, which in turn may allow e.g. increasing the velocity of the primary web and/or may allow reducing the probability of producing defective coated web. For example, the three-dimensional shape of the curtain may be stabilized by using one or more precisely controlled gas flows, wherein the flow rates of the gas flows may be adjusted based on the distance information.

In an embodiment, using the distance information may allow smart die-cutting, where a coated web may be effectively utilized also when the coated web comprises defective portions. This may minimize the amount of rejected material.

Using the method may allow producing a coated web, where the coating layer has a substantially constant thickness, i.e. the spatial variations may be very small. This may allow minimizing the amount of the coating material used for producing the coated web.

In an embodiment, the method may comprise forming a label web or a label laminate web in order to produce substantially transparent or translucent labels. Thanks to the method, the produced web may have spatially uniform visual appearance. In an embodiment, the thickness of the coating layer may be minimized, which in turn may improve the light-transmitting properties of the web.

In an embodiment, the instantaneous shape of the curtain may be monitored by simultaneously projecting a plurality of pointer features on the curtain, and by analyzing the images of the pointer features. In an embodiment, the three-dimensional instantaneous shape of the curtain may be monitored by simultaneously projecting a plurality of pointer features on the curtain, and by analyzing the images of the pointer features.

In an embodiment, an image of the curtain may be captured and analyzed in order to determine whether the curtain has a fully continuous surface or whether the curtain has one or more void portions. A void may be detected e.g. by using pixel value thresholding. The image of the curtain may be a greyscale image or a color image. The greyscale image or the color image may be analyzed e.g. by pixel value thresholding in order to detect a void. The reliability of detecting a void may be improved when the information obtained by the thresholding is supplemented with distance information. If the presence of the voids cannot be detected reliably, this may cause wasteful rejection of the coated web and/or this may cause quality problems.

A coated web produced by a curtain coating process may be associated with defect data obtained by monitoring the curtain during the curtain coating process. The defective portions of the coated web may be subsequently identified by using the defect data. The defective portions may be identified and cut away from the web. The defective portions may be rejected or used for less demanding applications. The remaining intact portions may be used normally e.g. for producing adhesive labels.

In an embodiment, monitoring the curtain may also be disturbed by a foreign object, which temporarily blocks the field of view of a monitoring unit. The foreign object may be e.g. a person who is performing a maintenance operation, or a tool held by the person. In an embodiment, the presence of the foreign object may be detected by using distance information. A coated web produced by a curtain coating process may be associated with surveillance data obtained by monitoring the curtain during the curtain coating process. The surveillance data may e.g. indicate when the presence of a foreign object was detected. The surveillance data may be provided e.g. based on distance information. The uninspected portions of the coated web may be subsequently identified by using the defect data. For example, the uninspected portions may be identified and treated separately. For example, the uninspected portions may be rejected, or used for a less demanding application.

BRIEF DESCRIPTION OF THE DRAWINGS

In the following examples, several variations will be described in more detail with reference to the appended drawings, in which.

DETAILED DESCRIPTION

Figure 1:
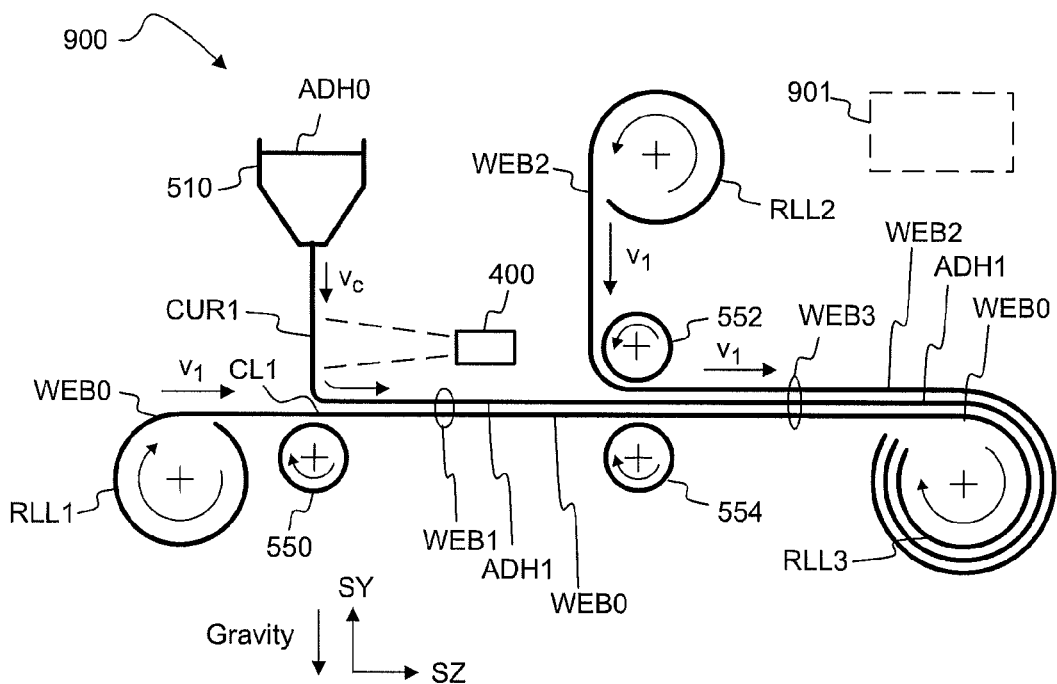
FIG. 1 shows, by way of example, in a side view, an apparatus for producing a coated web by curtain coating.

FIG. 1 shows a curtain coating apparatus 900, which may be arranged to produce e.g. a coated web WEB1 or a laminate web WEB3. The apparatus 900 may comprise a distributor unit 510, which may be arranged to form a layer CUR1, which comprises a coating material ADH0. The layer CUR1 may be called e.g. as a curtain or veil. The material ADH0 of the curtain CUR1 may be substantially in a liquid state. The material ADH0 of the curtain CUR1 may fall downwards towards a moving primary web WEB0 in order to form a coating layer ADH1 on the primary web WEB0. A coated web WEB1 may be produced by coating the moving primary web WEB0 with the coating layer ADH1. The coating layer ADH1 of the coated web WEB1 may be formed such that the material ADH0 of the curtain CUR1 at least temporarily adheres to the primary web WEB0.

The back surface of the curtain CUR1 may contact the primary web WEB0 at a contact line CL1. The primary web WEB0 may be moved at a velocity $v_1$ with respect to a stationary reference REF0. The stationary reference REF0 may be e.g. a predetermined point of the distributor unit 510. The coating layer ADH1 of the coated web WEB1 may comprise or consist of coating material ADH0, which covered the primary web WEB0 after falling from the distributor unit 510.

The primary web WEB0 and/or the coated web WEB1 may be supported by a supporting member 550. The supporting member 550 may be e.g. a roll, a conveyer belt or an air cushion unit. The supporting member 550 may be located beneath the contact line CL1. The primary web WEB0 and/or the coated web WEB1 may be directly or undirectly moved by a roll. The web WEB0, WEB1 may be moved e.g. by one or more of the rolls 550, 552, 554.

Figure 3A:
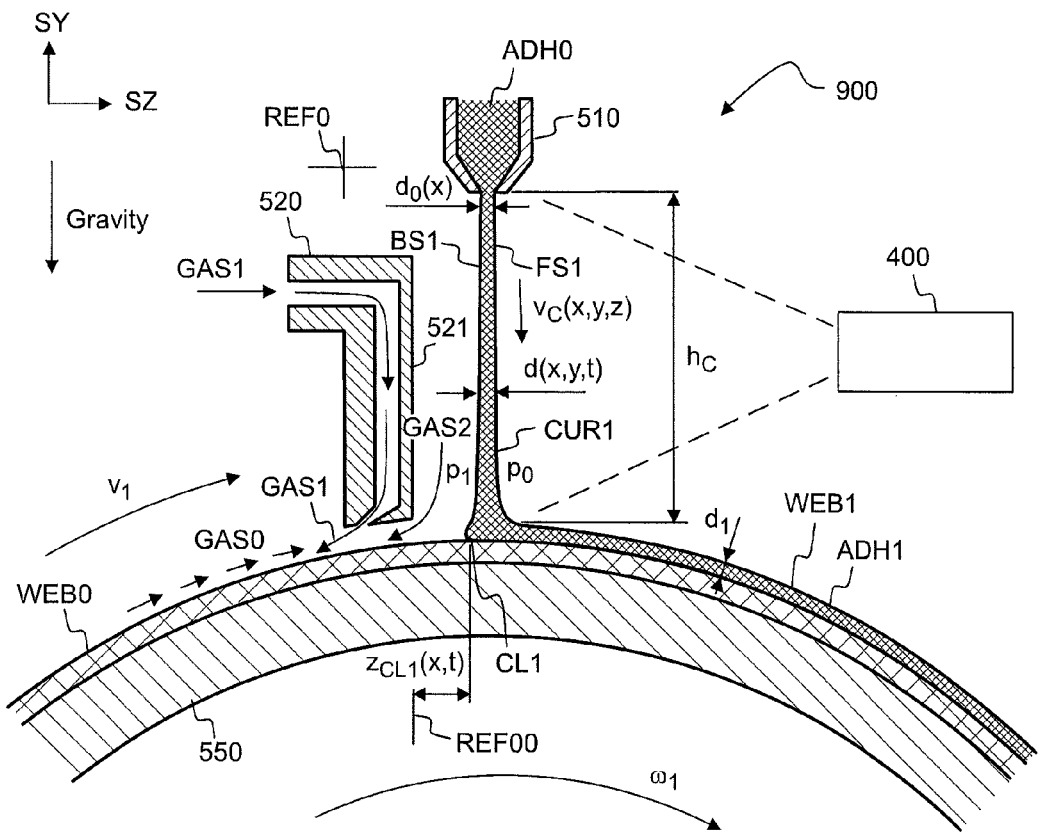
FIG. 3a shows, by way of example, in a side view, producing a coated web by curtain coating.

The curtain CUR1 may be located between a first gas-liquid interface and a second gas-liquid interface such that the material ADH0 may freely fall downwards e.g. due to gravity. The first gas-liquid interface may be called e.g. as the front surface FS1 of the curtain CUR1, and the second gas-liquid interface may be called e.g. as the back surface BS1 of the curtain CUR1 (FIG. 3a). During normal operation, the front surface FS1 of the curtain CUR1 may be substantially vertical.

The apparatus 900 may comprise a monitoring unit 400, which may be arranged to monitor the curtain CUR1 during curtain coating. The apparatus 900 may comprise a control system 901 for gathering measurement data from the monitoring unit 400, for processing the measurement data, and/or for controlling operation of the apparatus 900. In particular, the control system 901 may be arranged to control operation of the apparatus 900 based on measurement data obtained from the monitoring unit 400.

The coated web WEB1 may be optionally coated with a second web WEB2 in order to form a laminate web WEB3. The laminate web WEB3 may be produced by combining the coated web WEB1 with the second web WEB2 such that the coating layer ADH1 remains between the primary web WEB0 and the second web WEB2. The second web WEB2 may be optionally pressed against the coating layer ADH1 e.g. by compression rolls 552, 554.

The coating layer ADH1 may be optionally cured e.g. by heating and/or by using ultraviolet radiation. The coating layer ADH1 may be cured e.g. before laminating the coated web WEB1 with the second web WEB2.

The primary web WEB0 may be provided e.g. by unwinding a roll RLL1, or by obtaining the primary web WEB0 from an additional web processing unit. The second web WEB2 may be provided e.g. by unwinding a roll RLL2, or by obtaining the second web WEB2 from an additional web processing unit. The laminate web WEB3 or the coated web WEB1 may be e.g. reeled up to form a roll RLL3. The laminate web WEB3 or the coated web WEB1 may be optionally guided to a further processing step. The laminate web WEB3 or the coated web WEB1 may be optionally cut to form a plurality of sheets. The coated web WEB1 or the laminate web WEB3 may be cut into sheets e.g. by using die-cutting or laser cutting. One or more portions may be cut from the coated web WEB1 or the laminate web WEB3 by e.g. by using die-cutting or laser cutting.

Figure 4:
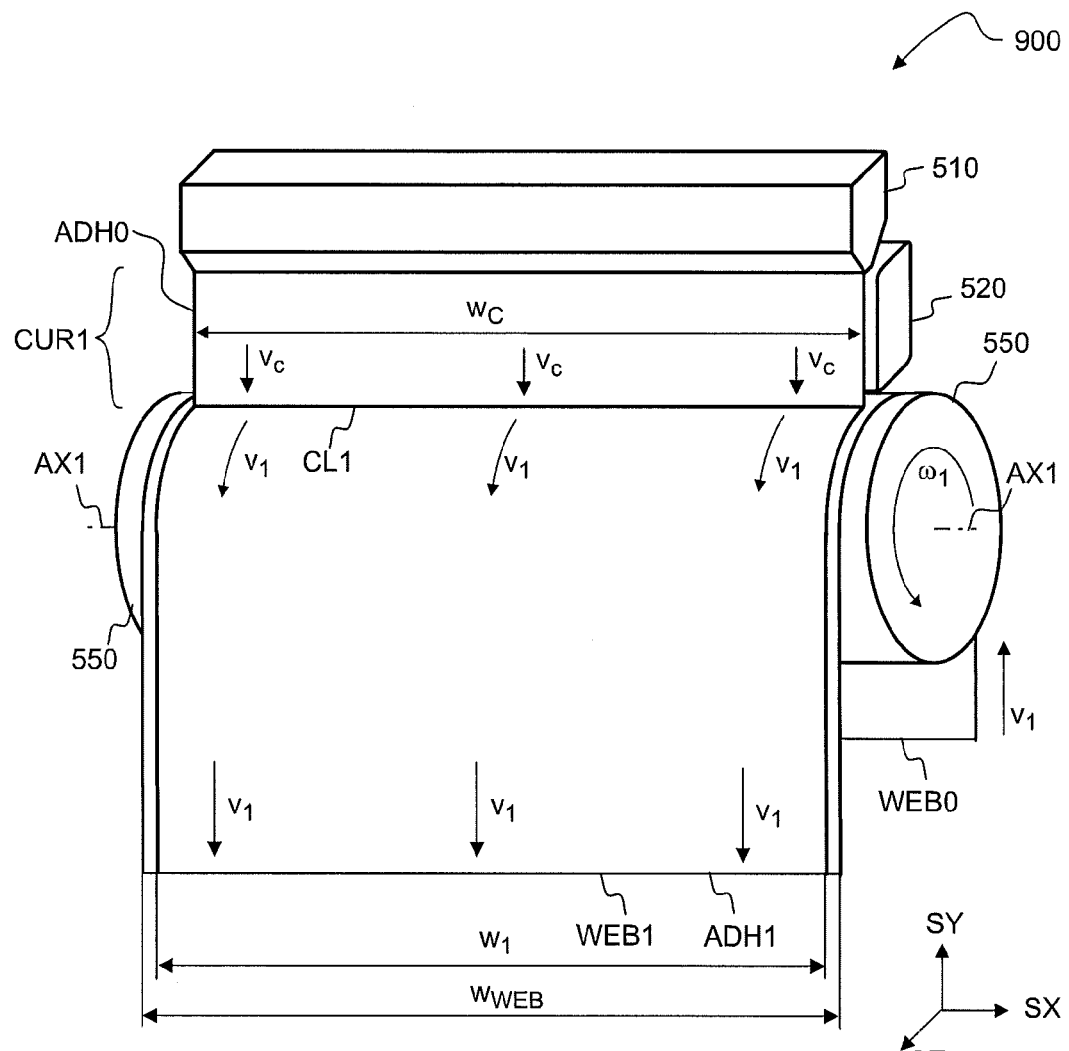
FIG. 4 shows, by way of example, in a three dimensional view, a curtain coating apparatus.

SX, SY and SZ denote orthogonal directions. The directions SX, SY and SZ define a coordinate system fixed to the apparatus 900. The direction SY may be anti-parallel with the direction of the gravity. The material of the curtain CUR1 may fall substantially in the direction of the gravity. The direction SX may be transverse to the direction of movement of the web WEB0 in the vicinity of the contact line CL1. The direction SX may be substantially perpendicular to the direction of movement of the web WEB0 in the vicinity of the contact line CL1. The contact line CL1 may be aligned with the direction SX. The coated web WEB1 may be supported by a roll 550, which has an axis AX1 of rotation, wherein the direction SX may be substantially parallel with the axis AX1 (FIG. 4). A position in the coordinate system may be defined by coordinates x,y,z, respectively.

The primary web WEB0 may comprise e.g. paper or plastic. The second web WEB2 may comprise e.g. paper or plastic. The WEB0, WEB2 may comprise e.g. polyester and/or polypropylene.

The apparatus 900 may be arranged to produce e.g. label web WEB1, or a label laminate web WEB3. The coating material ADH0 may comprise or consist of e.g. adhesive material. The adhesive material ADH0 may comprise e.g. polyurethane adhesive, and/or acrylic adhesive. The adhesive material ADH0 may consist of polyurethane adhesive and/or acrylic adhesive. The coating layer ADH1 of the coated web WEB1 may be arranged to operate e.g. as a pressure sensitive adhesive layer, as a heat-activatable adhesive layer, as a heat-curable adhesive layer, and/or as a radiation curable adhesive layer. The webs WEB0, WEB1, WEB2, WEB3 may be flexible.

The primary web WEB0 may be used e.g. as the carrier layer of a label web or as the carrier layer of a label laminate web, and the second web WEB2 may be used e.g. as a release liner of the label laminate web. The carrier layer may also be called e.g. as a feedstock layer. The release liner WEB2 may comprise e.g. plastic, paper or cardboard coated with an anti-adhesion agent. The release liner WEB2 may comprise an anti-adhesion layer, which comprises anti-adhesion agent. The anti-adhesion agent may comprise e.g. silicone and/or a fluoropolymer. One or more adhesive labels LABEL1 may be produced by cutting from the web WEB3, and by removing the release liner.

Alternatively, the primary web WEB0 may be used as a release liner of a label laminate web, and the second web WEB2 may be used e.g. as the carrier layer of the label laminate web. The release liner WEB2 may comprise an anti-adhesion layer, which comprises anti-adhesion agent. The anti-adhesion agent may comprise e.g. silicone and/or a fluoropolymer. The primary web WEB0 may comprise e.g. plastic, paper or cardboard coated with an anti-adhesion agent. One or more adhesive labels LABEL1 may be produced by cutting from the web WEB3, and by removing the release liner.

The thickness of the web WEB0, WEB1, WEB2 and/or WEB3 may be e.g. in the range of 0.01 mm to 0.5 mm, in particular in the range of 0.02 mm to 0.3 mm. In an embodiment, the WEB0, WEB1, WEB2 and/or WEB3 may be transparent or translucent.

The coating material ADH0 may also comprise or consist of an anti-adhesion agent. The anti-adhesion agent may comprise e.g. silicone and/or a fluoropolymer. The coating material ADH0 does not need to comprise an adhesive.

Figure 2A:
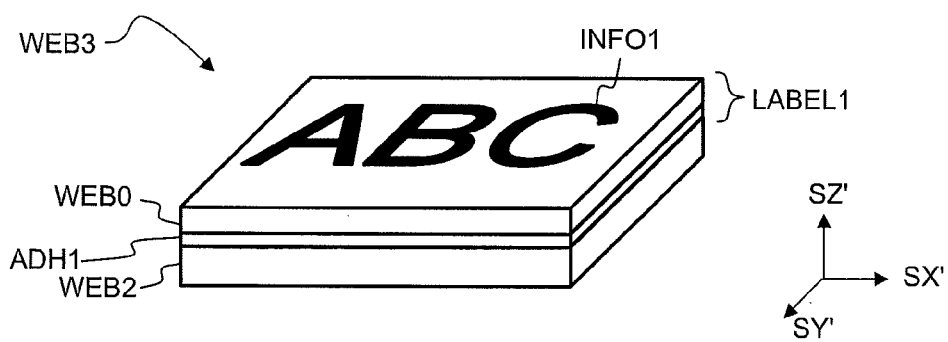
FIG. 2a shows, by way of example, in a three dimensional view, a label laminate web.

FIG. 2a shows a label laminate web WEB3, which may be obtained by curtain coating. The label laminate web WEB3 may comprise a carrier layer WEB0, an adhesive layer ADH1, and a release liner WEB2. The label laminate web WEB3 may comprise one or more visually detectable markings INFO1 produced in and/or on the carrier layer WEB0. The marking INFO1 may comprise e.g. text, a trade mark pattern, or a barcode.

The directions SX', SY' and SZ' define a coordinate system of the coated web WEB1, when the WEB1 is straightened so that it is substantially planar. The directions SX', SY' and SZ' are orthogonal. The direction SY' may denote the machine direction of the coated web WEB1, and SX' may denote the cross machine direction of the coated web WEB1. The term "machine direction" SY" means that the primary web WEB0 moved in the direction SY' in the vicinity of the contact line CL1 when the coating material ADH0 was brought into contact with the primary web WEB0.

Figure 2B:
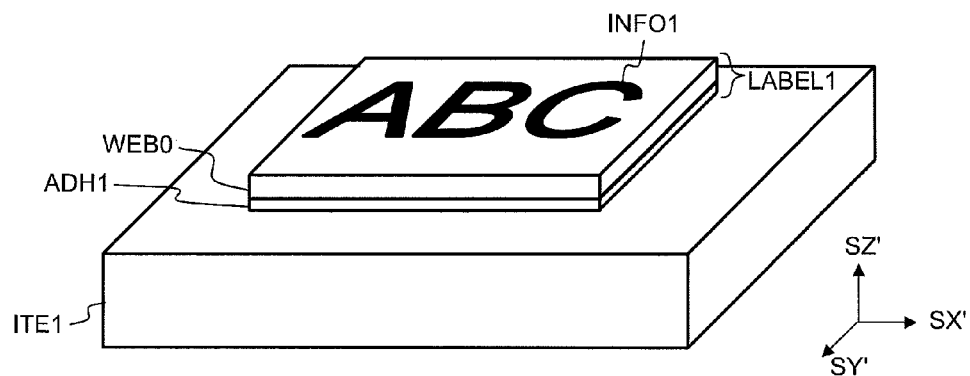
FIG. 2b shows, by way of example, in a three dimensional view, a label attached to an item.

FIG. 2b shows a label LABEL1 attached to an item ITE1. The item ITE1 may be e.g. container. The container may be e.g. a glass bottle, a plastic bottle or a cardboard box. The label LABEL1 attached to an item ITE1 e.b. by cutting a piece from the label laminate web WEB3 of FIG. 2a, peeling the release liner WEB2 away from the LABEL1, and bringing the LABEL1 into contact with the item ITE1 so that the LABEL1 sticks to the surface of the item ITE1. The label may be optionally pressed and/or heated in order to improve adhesion. The adhesive layer ADH1 may comprise adhesive ADH0, which may be e.g. pressure sensitive, thermally activatable, or UV curable.

In an embodiment, the adhesive layer ADH1 of the label web WEB2 does not need to be covered with a release liner. The label web may be stored and/or transported as a linerless label web WEB1. The linerless label may be activated e.g. by heat prior to attaching it to an item ITE1.

Figure 2C:
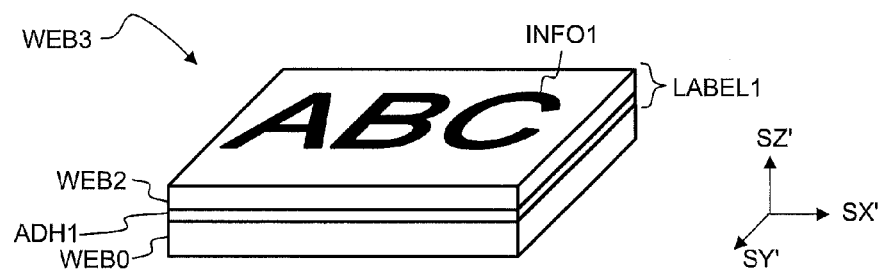
FIG. 2c shows, by way of example, in a three dimensional view, a label laminate web.

FIG. 2c shows a label laminate web WEB3, which may be obtained by curtain coating. The label laminate web WEB3 may comprise a carrier layer WEB2, an adhesive layer ADH1, and a release liner WEB0. The label laminate web WEB3 may comprise one or more visually detectable markings INFO1 produced in and/or on the carrier layer WEB0. The marking INFO1 may comprise e.g. text, a trade mark pattern, or a barcode.

Figure 2D:
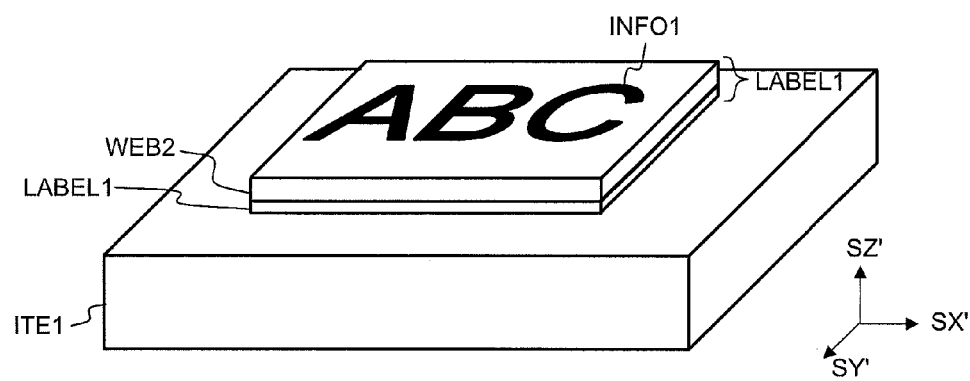
FIG. 2d shows, by way of example, in a three dimensional view, a label attached to an item.

FIG. 2d shows a label LABEL1 attached to an item ITE1. The item ITE1 may be e.g. container. The container may be e.g. a glass bottle, a plastic bottle or a cardboard box. The label LABEL1 attached to an item ITE1 e.b. by cutting a piece from the label laminate web WEB3 of FIG. 2c, peeling the release liner WEB0 away from the LABEL1, and bringing the LABEL1 into contact with the item ITE1 so that the LABEL1 sticks to the surface of the item ITE1. The label may be optionally pressed and/or heated in order to improve adhesion. The adhesive layer ADH1 may comprise adhesive ADH0, which may be e.g. pressure sensitive, thermally activatable, or UV curable.

FIG. 3a shows the curtain CUR1 and the coated web WEB1 in a cross-sectional side view. The coating material ADH0 of the curtain CUR1 may substantially continuously fall downwards e.g. due to gravity, due to a pulling force created by the moving web WEB0, and/or due to inertia of the coating medium ADH0 discharged from the distributing unit 510. The primary web WEB0 may be moved in a direction, which is transverse to the direction of gravity. The back surface BS1 of the curtain CUR1 may contact the primary web WEB0 at a contact line CL1. The coating apparatus 900 may be arranged to operate e.g. such that the contact line CL1 is substantially straight. However, the shape of the curtain CUR1 may momentarily deviate from the substantially planar form e.g. due to instable flow of the material ADH0 through the distributor unit 510, due to fluctuations caused by a fluctuating pressure difference $p_1-p_0$ over the curtain CUR1 and/or due to fluctuations caused by a pulling (cohesive) force created by the moving coating layer ADH1. Thus, the contact line CL1 may be straight or curved depending on the momentary shape of the curtain CUR1.

$z_{CL1}(x,t)$ denotes a horizontal distance between contact line CL1 and a reference plane REF00 at a lateral position x and at the time t. The contact line CL1 may be substantially parallel to the direction SX (FIG. 4). The distributor unit 510 may comprise e.g. shelf structure and/or a nozzle for forming the curtain CUR1. The curtain CUR1 may have an initial thickness $d_0(x)$ at the lateral position x. The material ADH0 of the curtain CUR1 may fall at each point (x,y,z) a velocity $v_C(x,y,z)$. The front surface FS1 of the curtain CUR1 may have a height $h_C$. The curtain CUR1 may have an instantanous thickness $d(x,y,t)$ at each position $(x,y)$ at a time t.

The primary web WEB0 and the coated web WEB1 may be supported e.g. by the roll 550. $v_1$ denotes the velocity of the primary web WEB1 at the contact line CL1. $v_1$ denotes the velocity of the uncovered primary web WEB0 with respect to a stationary reference REF0. The velocity $v_1$ of the primary web WEB0 may be e.g. in the range of 0.5 m/s to 60 m/s. The velocity $v_1$ of the primary web WEB0 may be e.g. in the range of 5 m/s to 40 m/s. The velocity $v_1$ of the primary web WEB0 may be e.g. in the range of 0.5 m/s to 5 m/s. Using a lower velocity $v_1$ may improve stability of the curtain CUR1.

The roll 550 may be rotated at an angular velocity $\omega_1$ so that the primary web WEB0 may move at the velocity $v_1$. The velocity of the coated web WEB1 may be substantially equal to the velocity $v_1$ of the primary web WEB0. The curtain coating may be performed substantially without stretching the primary web WEB0. If the method comprises forming a laminate web WEB3, the temporally averaged velocity of the laminate web WEB3 may be substantially equal to the temporally averaged velocity $v_1$ of the primary web WEB0.

The moving surface of the primary web WEB0 may create a moving layer of gas GAS0. The moving layer of gas GAS0 may be called e.g. as a boundary layer GAS0. The gas flow GAS0 may potentially cause deformation of the curtain CUR1. The gas flow GAS0 may potentially cause random and/or periodic oscillation of the curtain CUR1, which in turn may cause a spatially non-uniform thickness $d_1$ of the coating ADH1. The boundary layer GAS0 may cause e.g. formation of gas bubbles between the primary web WEB0 and the coating layer ADH1. The apparatus 900 may optionally comprise a gas flow stabilizing unit 520 for controlling the pressure difference $p_1 - p_0$ over the curtain CUR1. $p_1$ denotes local pressure at the front surface FS1 of the curtain CUR1. $p_0$ denotes local pressure at the back surface BS1 of the curtain CUR1. The pressure difference $p_1 - p_0$ may cause deflection and/or deformation of the curtain CUR1. The stabilizing unit 520 may reduce or control the gas flow GAS0. A gas flow GAS1 of the stabilizing unit 520 may be arranged to minimize or prevent formation of the air bubbles. In an embodiment, the stabilizing unit 520 may be arranged to cause a secondary air flow GAS2 e.g. in order to control the pressure $p_0$ between the curtain CUR1 and the stabilizing unit 520. The marking GAS2 may also denote gas, which is in contact with the curtain CUR1 and with the primary WEB0.

The curtain CUR1 may be optically monitored by a monitoring unit 400. The monitoring unit 400 may be arranged to monitor the deflection and/or deformation of the curtain CUR1. The monitoring unit 400 may be arranged to detect deflection and/or deformation of the curtain CUR1. The monitoring unit 400 may be arranged to measure a distance between the monitoring unit 400 and the curtain CUR1, and the monitoring unit 400 may also be called e.g. as a distance sensor unit. The monitoring unit 400 may be arranged to measure deflection and/or deformation of the curtain CUR1. The monitoring unit 400 may be arranged to measure an instantaneous three-dimensional shape of the curtain CUR1. The monitoring unit 400 may be arranged to measure an instantaneous three-dimensional shape of the front surface FS1 of the curtain CUR1. The monitoring unit 400 may be arranged to detect whether the curtain has one or more voids.

The stabilizing unit 520 may have a front surface 521. In an embodiment a predetermined point of the stabilizing unit 520 may be used as a reference point REF0. The reference point REF0 may be in the field of view of the monitoring unit 400. In an embodiment, the front surface 521 may be substantially planar, and the front surface 521 may define the reference plane REF00. A part of the front surface 521 may be in the field of view of the monitoring unit 400 e.g. when the curtain is absent and/or when the monitoring unit 400 detects the front surface 521 through a void.

Figure 3B:
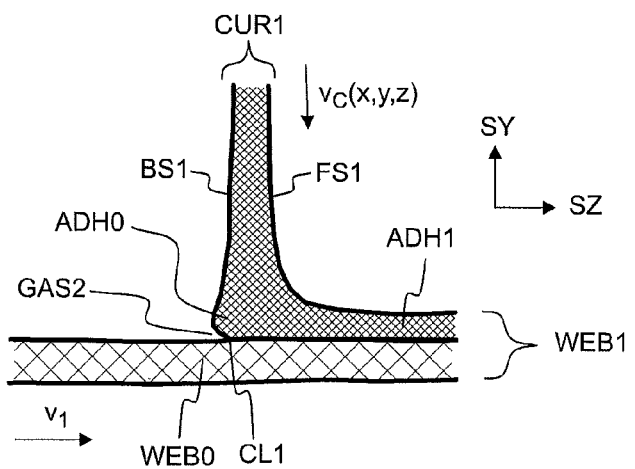
FIG. 3b shows, by way of example, in a side view, the contact line where the curtain meets the primary web.

Referring to FIG. 3b, the curtain CUR1 may meet the primary web WEB0 at the contact line CL1. The contact line CL1 may be defined by the primary web WEB0 and the curtain CUR1. The coating material ADH0 of the curtain CUR1 may be brought into contact with the primary web WEB0 at the contact line CL1. The back side BS1 of the curtain CUR1 may represent a gas-liquid interface between a gas GAS2 and the coating material ADH0. The position of the contact line CL1 may be defined by the gas GAS2, by the primary web WEB0, and by the coating material ADH0 of the curtain CUR1. Three different phases may meet at the contact line CL1. The gas GAS0, the surface of the primary web WEB0, and the coating material ADH0 may meet at the contact line CL1. The coating material ADH0 of the curtain CUR1 may move substantially downwards with respect to the contact line CL1. The primary web WEB0 may move with respect to the contact line CL1. The velocity of the primary web WEB0 with respect to the contact line CL1 may be substantially equal to the velocity $v_1$ of the primary web WEB0 with respect to a stationary reference. However, the velocity of the primary web WEB0 with respect to the contact line CL1 may temporarily be slightly different from the velocity $v_1$, because the position of the contact line CL1 may move according to the deflections and/or deformations of the curtain CUR1.

FIGS. 1, 3a and 3b illustrate some examples of curtain coating arrangements, some effects related to the behavior of the curtain flow, and some parameters related to the behavior of the curtain flow. The coating arrangements may be varied e.g. depending on the properties of the primary web WEB0 and/or depending on the properties of the coating material ADH0.

FIG. 4 shows, in a three dimensional view, the coating apparatus 900. The primary web WEB0 may be supported e.g. by a roll 550. The contact line CL1 may be substantially parallel to an axis AX1 of rotation of the roll 550. The width $w_1$ of the coating layer ADH1 of the coated web WEB1 may be e.g. in the range of 0.5 m to 4.0 m. The curtain CUR1 may have a width $w_C$. The width $w_C$ may be substantially equal to the width $w_1$. The web WEB0, WEB1 may have a width $W_{WEB}$. The width $w_{WEB}$ may be greater than or equal to the width $w_1$. The width $w_{WEB}$ may be e.g. in the range of 0.5 m to 4.0 m. The width $w_1$ of the coating layer ADH1 of the coated web WEB1 may be e.g. in the range of 0.5 m to 15 m. The width $w_{WEB}$ of the web may be e.g. in the range of 0.5 m to 15 m.

Figure 5A:
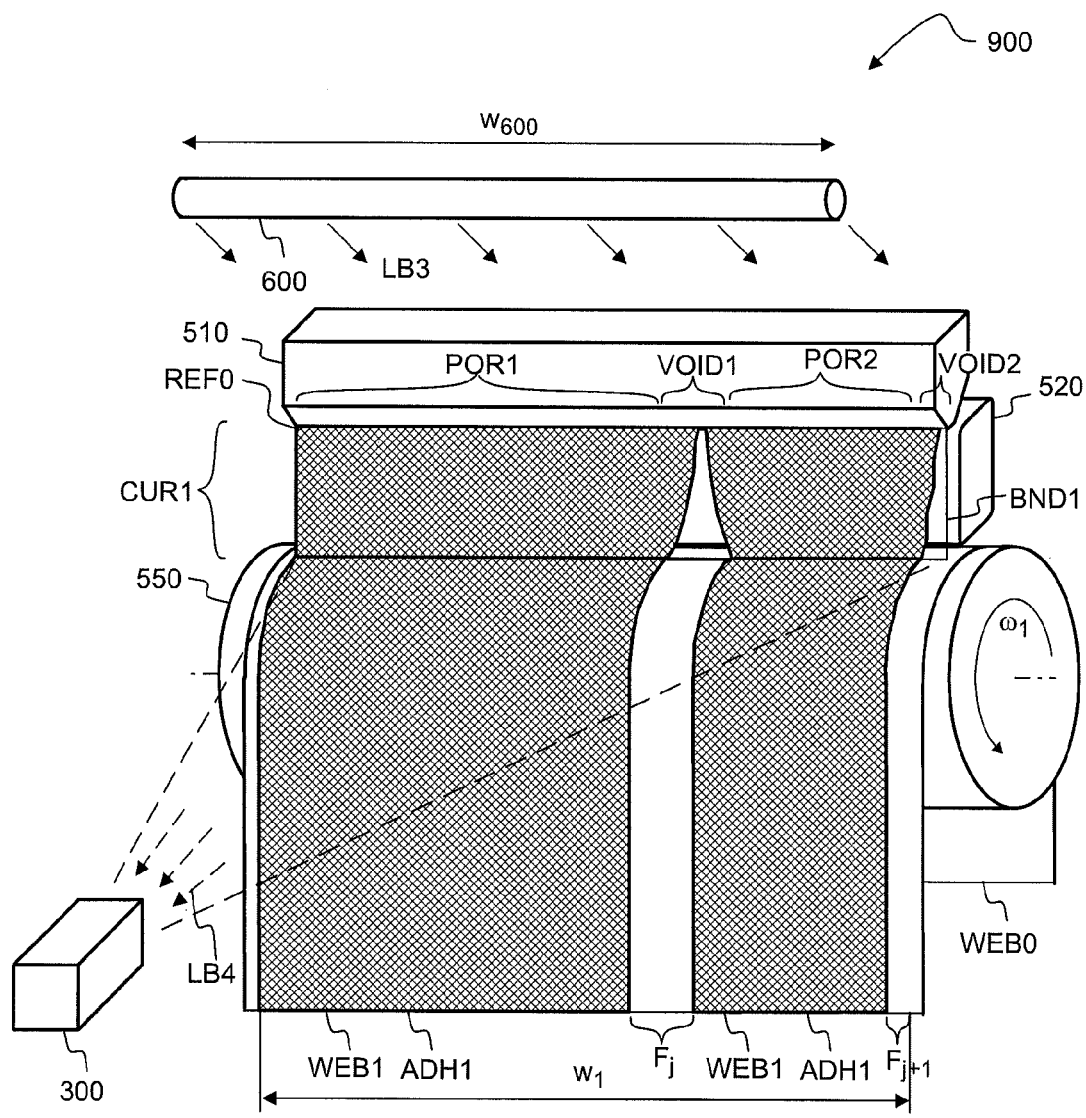
FIG. 5a shows, by way of example, in a three dimensional view, monitoring a curtain by an imaging unit.

Referring to FIG. 5a, the curtain CUR1 may momentarily have one or more void portions VOID1, VOID2, which do not comprise the coating material ADH0, or where the thickness $d(x,y,t)$ of the curtain is abnormally low. The void portions VOID1, VOID2 may be called e.g. as voids or holes.

The curtain CUR1 may have a normal boundary BND1. The normal boundary BND1 may be defined by the perimeter of the curtain CUR1 during normal operation. A void portion VOID1, VOID2 may be a portion which is located within the normal boundary BND1, but which does not comprise the coating material ADH0.

The curtain CUR1 may have a normal thickness $d_{REF}(x,y)$ at each location (x,y) within the normal boundary BND1. The thickness $d_{REF}(x,y)$ does not need to be spatially constant. The curtain CUR1 may have an instantaneous thickness d(x,y,t) at each location (x,y) within the normal boundary BND1. The curtain CUR1 may momentarily have one or more thin portions where the instantaneous thickness d(x,y,t) is substantially lower than the normal thickness $d_{REF}(x,y)$ of the curtain CUR1. In an embodiment, the term "void portion" may also refer to a thin portion. The term "void portion" may refer to a portion, where the instantaneous thickness d(x,y,t) of the curtain CUR1 is substantially lower than the normal thickness $d_{REF}(x,y)$ of the curtain CUR1.

The voids VOID1, VOID2 may be caused e.g. by the instability of the curtain CUR1, due to a locally blocked distributor unit 510 and/or due to wrong operating parameters of the coating apparatus 900. The coated web WEB1 may comprise one or more defective portions $F_j$, $F_{j+1}$ (see FIG. 14a) where the coating material ADH0 may be missing or where the thickness $d_1$ of the coating layer ADH1 may be abnormally low. The lateral positions of the defect portions $F_j$, $F_{j+1}$ may correspond to the lateral positions of the voids VOID1, VOID2. The lateral positions of the defect portions $F_j$, $F_{j+1}$ may be determined by monitoring the lateral positions of the voids VOID1, VOID2. The longitudinal positions of the defect portions $F_j$, $F_{j+1}$ may be determined by monitoring with sufficient temporal resolution when the voids VOID1, VOID2 are present, and by using the known velocity $v_1$ of the primary web WEB0.

The curtain CUR1 may comprise one or more continuous portions POR1, POR2 where the thickness of the curtain is substantially equal to a normal value. The curtain CUR1 may comprise one or more continuous portions POR1, POR2 where the thickness of the curtain is greater than or equal to a threshold value.

The presence of the voids VOID1, VOID2 may be monitored e.g. by illuminating the curtain CUR1 with illuminating light LB3, and by capturing one or more images FRAME2 of the curtain by an imaging unit 300. The illuminating light LB3 may be provided by an illuminating unit 600.

The illuminating unit 600 may comprise e.g. a fluorescent lamp, one or more light emitting diodes (i.e. LEDs), one or more lasers and/or one or more gas discharge lamps (e.g. a xenon flash lamp). The illuminating unit 600 may comprise a light-emitting surface whose width $w_{600}$ is greater than or equal to 50% of the width $w_1$ of the coating layer ADH1 of the coated web WEB1. The illuminating light LB3 may be e.g. visible light. In an embodiment, at least 50% of the optical power of the light LB3 may be in the wavelength range of 400 nm to 760 nm.

The illuminating unit 600 may be arranged to illuminate the curtain CUR1 with the illuminating light LB3 such that the spatial intensity distribution of the light LB3 at the front surface of the curtain CUR1 is substantially uniform. The width $W_{600}$ may be greater than or equal to 100% of the width $w_1$ of the coating layer ADH1 of the coated web WEB1. The illuminating unit 600 may comprise a light emitting surface, wherein the width $W_{600}$ of the light emitting surface may be greater than or equal to the width $w_C$ of the curtain CUR1, and the transverse dimension of the light emitting surface may be greater than or equal to the height $h_C$ of the curtain CUR1. The transverse dimension may be defined in a direction perpendicular to the direction SX. The light emitting surface may be implemented e.g. by a transmissive or reflective optical diffuser and/or by using a plurality of light sources arranged in a one-dimensional or two-dimensional array. The illuminating light LB3 may be pulsed or continuous. In case of pulsed light, the operation of the imaging unit 300 may be syncronized with the pulses of the illuminating light LB3.

In an embodiment, the illuminating unit 600 may illuminate the curtain CUR1 also in a non-uniform but temporally stable manner. In this case, the threshold values for detecting a void may depend on the position (x,y). The threshold values may be stored in a memory e.g. as pixel values of a reference image. In this case, the reference image may be called e.g. as a normalization image or as a threshold value image. The normalization image may be determined e.g. by temporarily placing a light-scattering (dummy) sheet to the position of the curtain CUR1, illuminating the dummy sheet with the (non-uniform) illumination, and by capturing a digital image of the sheet. During normal operation, the pixel values of a captured image FRAME2 may be optionally normalized by using the normalization image.

The layer CUR1 may provide reflected light LB4 by reflecting the illuminating light LB3. The refelcted light LB4 may be provided e.g. by scattering from the material of the layer CUR1, by specular reflection from the surface FS1, and/or by specular reflection from the surface BS1.

Figure 5B:
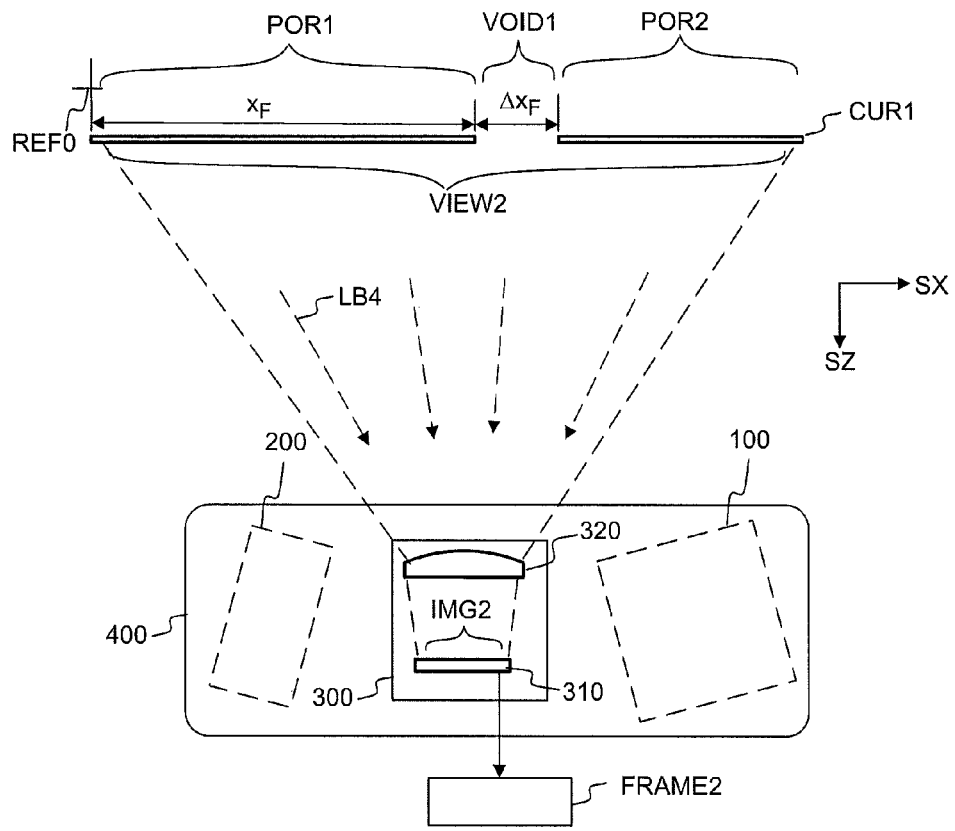
FIG. 5b shows, by way of example, in a top view, monitoring the curtain by an imaging unit.

Referring to FIG. 5b, the monitoring unit 400 may comprise an imaging unit 300, which may be arranged to detect the presence of voids VOID1, VOID2. The voids VOID1, VOID2 may be detected by analyzing an image FRAME2 captured by the imaging unit 300, e.g. by using pattern recognition. The imaging unit 300 may comprise imaging optics 320 and an image sensor 310. The imaging optics 320 may be arranged to form an optical image IMG2 on the image sensor 320 by focusing light LB3 reflected from the curtain CUR1. The image sensor 320 may be arranged to convert the optical image IMG2 into a digital image FRAME2. The digital image FRAME2 may also be called e.g. as an image frame.

In an embodiment, the imaging unit 300 may be selectively sensitive to visible light. The imaging unit 300 may be arranged to operate such that it is substantially insensitive to spectral components at wavelengths longer than 760 nm.

The image sensor 310 may comprise a two-dimensional array of detector pixels. The image sensor 310 may be e.g. CMOS image sensor or a CCD image sensor. The image sensor 310 may be e.g. a monochrome image sensor or RGB image sensor. The imaging unit 300 may be sensitive to visible light LB4.

The imaging unit 300 may have a field of view VIEW2. $x_F$ may denote the lateral position of the void VOID1 with respect to a location reference REF0. $\Delta x_F$ may denote the width of the void VOID1 when determined on the surface of the primary web WEB0.

The monitoring unit 400 may further comprise a projecting unit 200 and a second imaging unit 100 for measuring distances by triangulation.

Figure 5C:
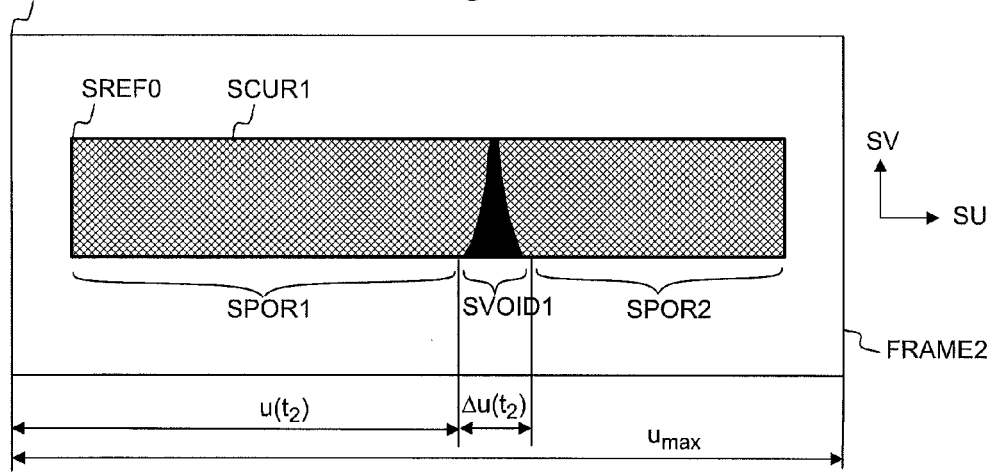
FIG. 5c shows, by way of example, a digital image of the curtain.

FIG. 5c shows an image frame FRAME2 provided by the imaging unit 300. The image frame FRAME2 may be a digital image corresponding to an optical image IMG2 formed at a time $t_2$. The image frame FRAME2 may comprise an image SCUR1 of the curtain CUR1. The image frame FRAME2 may comprise an image SPOR1 of a first continuous portion POR1 of the curtain CUR1. The image frame FRAME2 may comprise an image SPOR2 of a second continuous portion POR2 of the curtain CUR1. The image frame FRAME2 may comprise an image SVOID1 of the void portion VOID1. The image frame FRAME2 may comprise a point SREF0, which corresponds to the reference position REF0.

The images SCUR1, SPOR1, SPOR2, SVOID1 may also be called e.g. as sub-images. The presence of the image SVOID1 of the void portion VOID1 may be determined e.g. by using an image recognition algorithm. The boundaries of the image SVOID1 of the void portion VOID1 may be determined e.g. by using an image recognition algorithm. The boundaries of the image SVOID1 of the void portion VOID1 may be determined e.g. by using signal level thresholding. The digital image FRAME2 may comprise a plurality of image pixels such that each image pixel has a signal value. If the signal value of a pixel is lower (or higher) than a predetermined threshold value, said pixel may be determined to overlap the image SVOID1 of a void portion VOID1. The position $u(t_2)$ of the sub-image SVOID1 with respect to the reference position ORIG2 may be determined by analyzing the digital image FRAME2. The reference position ORIG2 may be e.g. at a predetermined corner of the image FRAME2 or at the point SREF0. The width $\Delta u(t_2)$ of the sub-image SVOID1 may be determined by analyzing the digital image FRAME2. $u_{max}$ may denote the total width of the digital image FRAME2. The width $u_{max}$ may be expressed e.g. as a number of pixels. $u_{max}$ may be e.g. in the range of 100 pixels to 10000 pixels.

The values of $u(t_2)$ and $\Delta u(t_2)$ may be expressed e.g. as a number of pixels (for example $u(t_2)$ may be equal to 100 pixels) or as relative values (for example $u(t_2)$ may be equal to 55% of $u_{max}$).

The directions SU and SV may define a coordinate system of the image frame FRAME2. The direction SU may correspond to the direction SX of the real space (i.e. the direction SU may a be an image of the direction SX). The direction SV may correspond to the direction SY of the real space.

The position of the void VOID1 may be determined based on the position of the sub-image SVOID1. The lateral position $x'_j$ of a defect portion $F_j$ (see FIG. 14a) caused by the void VOID1 may be determined based on the position $u(t_2)$ of the sub-image SVOID1 of the void VOID1.

The image frame FRAME2 may be optionally stored in a memory. The image frame FRAME2 may be used at a later stage e.g. as a documentation image.

Figure 6:
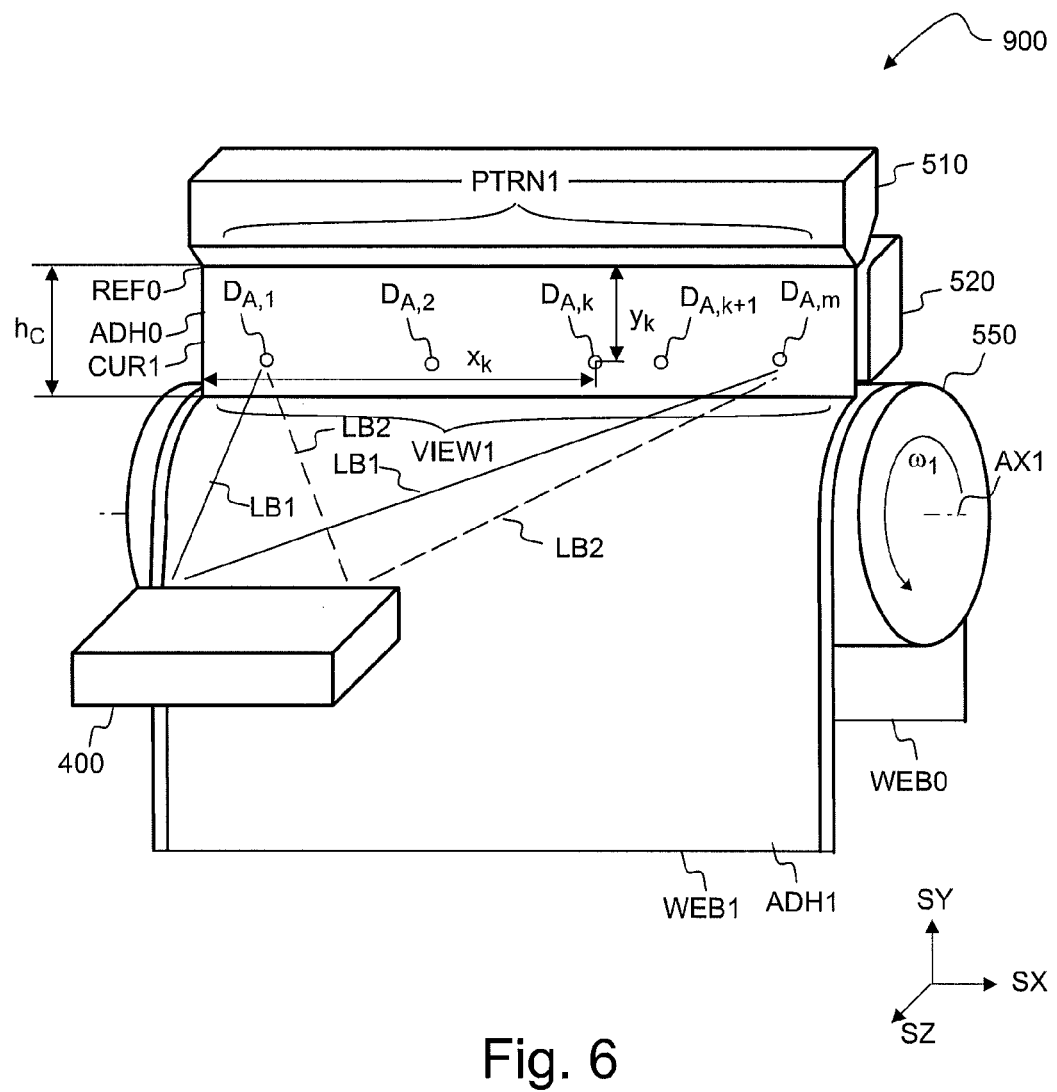
FIG. 6 shows, by way of example, in a three dimensional view, monitoring the curtain by a monitoring unit.

Referring to FIG. 6, a monitoring unit 400 may be arranged to provide distance information. The monitoring unit 400 may be arranged to measure distances to one or more pointer features $D_{A,1}$, $D_{A,2}$, $D_{A,k}$, $D_{A,k+1}$, $D_{A,m}$ by triangulation. The monitoring unit 400 may comprise a projecting unit 200, which may be arranged to project a pattern PTRN1 on the curtain CUR1. The projected pattern PTRN1 may comprise e.g. one or more pointer features $D_{A,1}$, $D_{A,2}$, $D_{A,k}$, $D_{A,m}$. The pointer features $D_{A,1}$, $D_{A,2}$, $D_{A,k}$, $D_{A,m}$ may be e.g. substantially circular spots, elliptical spots, or line sections. In an embodiment, the spots may be dots.

The pointer features may be projected on the curtain CUR1 by providing illuminating light beams LB1, which impinge on the curtain CUR1. In other words, the curtain CUR1 may operate as a display screen, which consists of a falling liquid film. The monitoring unit 400 may be arranged to receive light LB2 reflected from the curtain CUR1. The reflected light LB2 may be provided e.g. by scattering, which takes place within the material ADH0 of the curtain CUR1. For example, the material ADH0 may comprise particles, which scatter light. The material ADH0 may comprise a heterogeneous mixture, which is arranged to scatter light.

In particular, the material ADH0 may be selected such that the material ADH0 scatters light at the wavelength $\lambda_1$ of the projected light beams LB1. The wavelength $\lambda_1$ may be e.g. in the infrared region. The wavelength $\lambda_1$ may be e.g. in the range of 780 nm to 3000 nm. The material ADH0 may comprise light-scattering particles. The material ADH0 may be e.g. an adhesive composition, which comprises e.g. polyester segments and/or filler material particles to enhance scattering.

In an embodiment, the directions of the illuminating light beams LB1 may be selected such that the reflected light LB2 may be provided by specular reflection, which takes place at the front surface FS1 of the curtain CUR1. The reflected light LB2 may also be provided by specular reflection, which takes place at the back surface BS1 of the curtain CUR1.

The position of each pointer feature may be defined by coordinates x and y. For example, the position of the pointer feature $D_{A,k}$ may be defined by the coordinates $x_k$ and $y_k$.

Figure 7A:
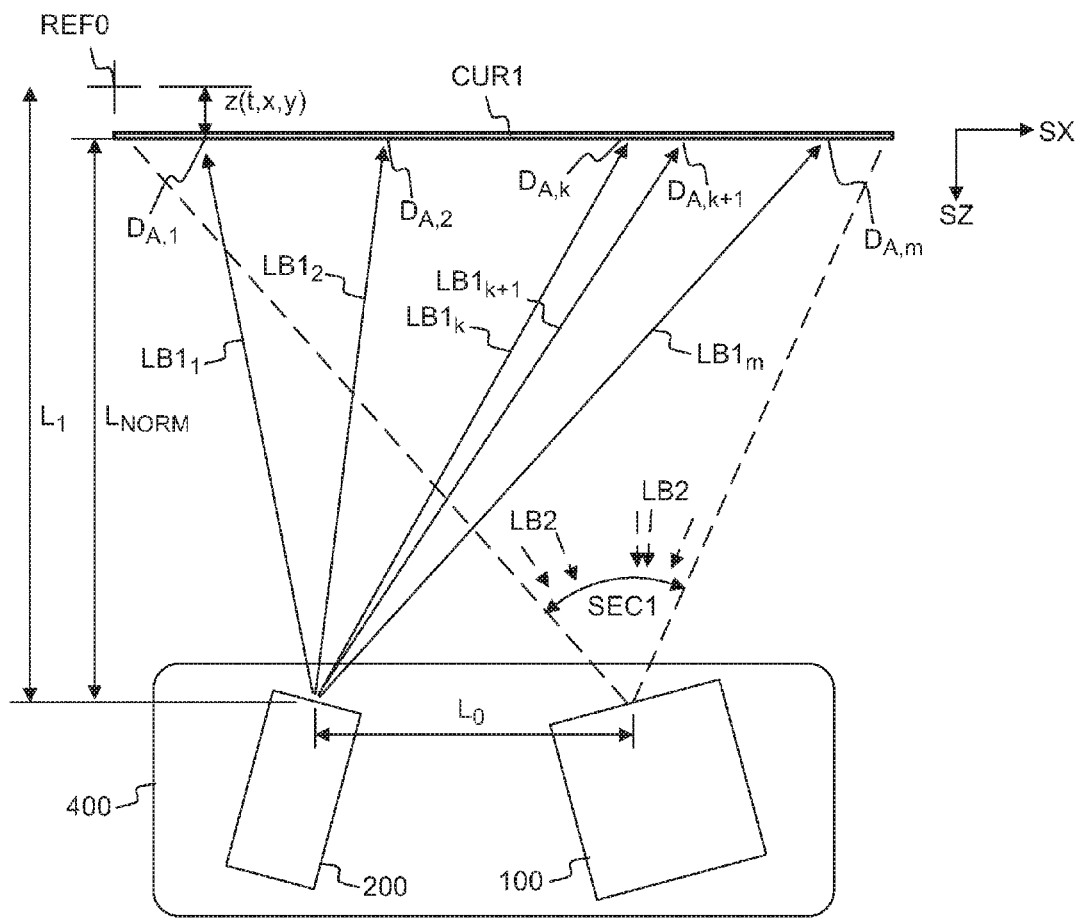
FIG. 7a shows, by way of example, in a top view, monitoring the curtain by a monitoring unit.

Referring to FIG. 7a, the monitoring unit 400 may comprise a projecting unit 200, which may be arranged to project one or more illuminating light beams $LB1_1$, $LB1_2$, $LB1_k$, $LB1_{k+1}$, $LB1_m$ such that the beams may impinge on the curtain CUR1 at the locations of the features $D_{A,1}$, $D_{A,2}$, $D_{A,k}$, $D_{A,k+1}$, $D_{A,m}$. The light LB1 may comprise one or more beams $LB1_1$, $LB1_2$, $LB1_k$, $LB1_{k+1}$, $LB1_m$. The curtain CUR1 may be arranged to provide reflected light LB2 by reflecting and/or scattering light of the light beams LB1. The pointer features $D_{A,1}$, $D_{A,2}$, $D_{A,k}$, $D_{A,k+1}$, $D_{A,m}$ are formed by the reflecting and/or scattering, which takes place at the locations of said features. The monitoring unit 400 may be arranged to measure the position of one or more pointer features $D_{A,1}$, $D_{A,2}$, $D_{A,k}$, $D_{A,k+1}$, $D_{A,m}$ by receiving light LB2 reflected from the curtain CUR1. The position of a pointer feature $D_{A,k}$ may be expressed e.g. by a horizontal coordinate $x_k$ and by a vertical coordinate $y_k$. The coordinates $x_k$ and $y_k$ may define the position of the pointer feature $D_{A,k}$ e.g. with respect to a reference point REF0. The reference point REF0 may be e.g. at a prominent feature of the apparatus 900, e.g. at a predetermined point of the distributor unit 510 or at a predetermined point of the stabilizing unit 520.

The monitoring unit 400 may comprise an imaging unit 100, which may have a field of view VIEW1 and a viewing sector SEC1. $L_0$ may denote a distance between the projecting unit 200 and the imaging unit 100 of the monitoring unit 400. $L_1$ may denote a distance between the principal point PP1 of the imaging unit 100 and a reference plane, which includes the reference point REF0. The reference plane may be defined e.g. by the directions SX, SY. In particular, $L_1$ may denote a distance between the principal point PP1 of the imaging unit 100 and the surface 521 of the gas flow stabilizing unit 520 (see FIG. 3a). The width of the field of view VIEW1 at the location of the curtain CUR1 may be e.g. greater than or equal to the width w1 of the coating layer ADH1 of the coated web WEB1. The three-dimensional shape of the curtain may be defined e.g. by a shape function $z(t,x,y)$. The shape function $z(t,x,y)$ may be time-dependent. The shape function $z(t,x,y)$ may define the position of the curtain CUR1 in the direction SZ as the function of time t and as the function of the coordinates x and y. The monitoring unit 400 may be arranged to measure the shape of the curtain CUR1. The monitoring unit 400 may be arranged to measure the instantaneous shape of the curtain CUR1 substantially in real time. $L_{NORM}$ may denote a normal distance between the layer CUR1 and the principal point PP1 of the imaging unit 100.

Figure 7B:
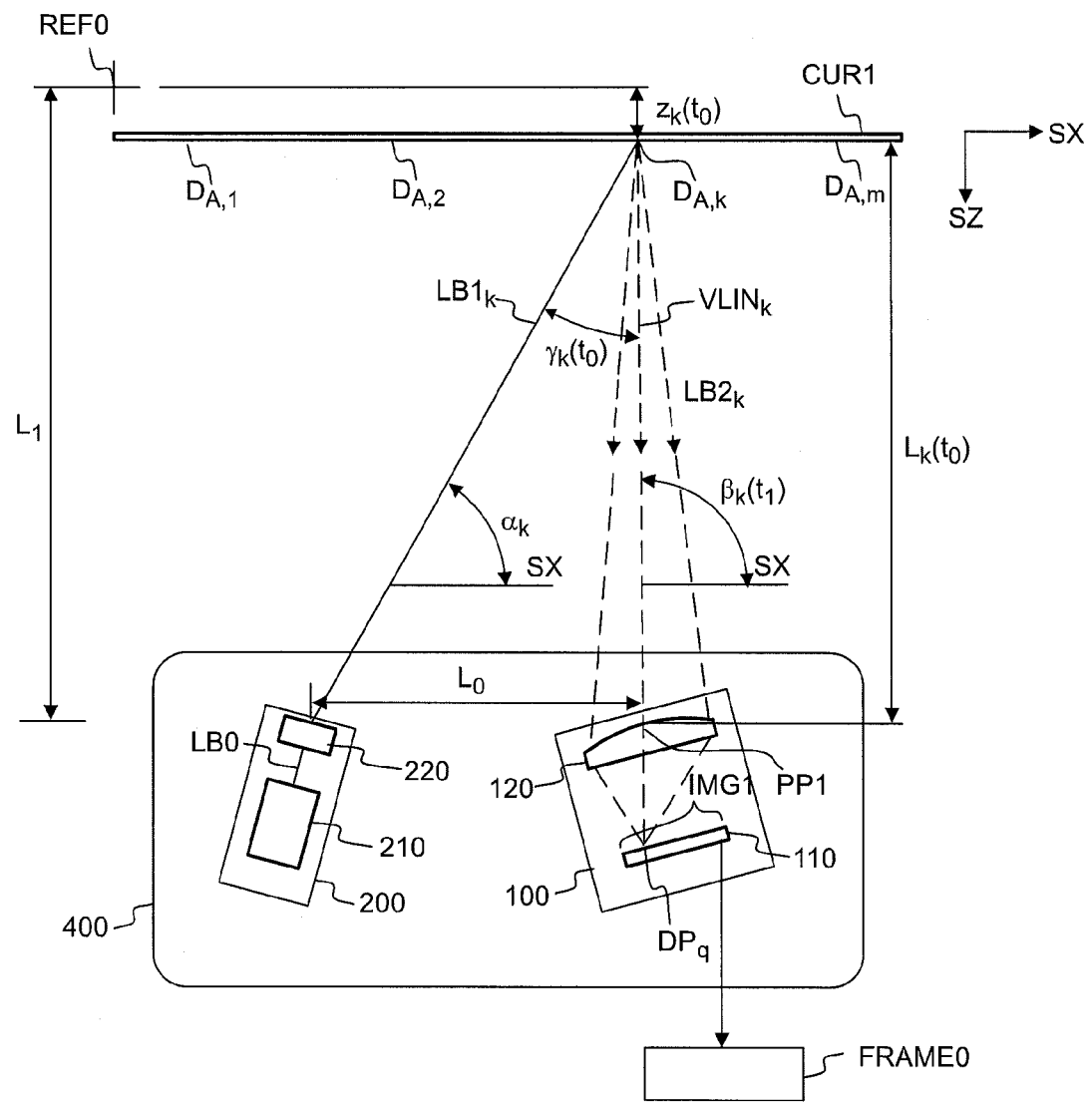
FIG. 7b shows, by way of example, in a top view, capturing an image of a projected feature in a reference state.

FIG. 7b illustrates capturing an image $SD_{A,k}$ of a pointer feature $D_{A,k}$ in a reference situation prevailing at a time $t_0$. The reference situation may refer e.g. to a situation where the curtain CUR1 is substantially planar. The reference situation may refer e.g. to a situation where the curtain CUR1 has a temporally stable shape.

The projecting unit 200 may comprise e.g. a light source 210 arranged to provide a primary beam LB0, and an optical element 220 arranged to provide one or more illuminating light beams LB1 by deflecting light of the primary beam LB0. The deflection may comprise deflection by diffraction, deflection by refraction and/or deflection by reflection.

In particular, the light source 210 may comprise e.g. a laser arranged to provide a laser beam LB0. The optical element 220 may be e.g. a holographic element or a diffraction grating, which may be arranged to provide several illuminating light beams LB1 by diffracting light of the laser beam LB0 such that the light beams LB1 may simultaneously propagate in different directions. One of the light beams LB1 may be marked e.g. with the symbol $LB1_k$. The curtain CUR1 may form the pointer feature $D_{A,k}$ by reflecting and/or scattering light of the beam $LB1_k$. Thus, the pointer feature $D_{A,k}$ may be formed at the location where the beam $LB1_k$ impinges on the curtain CUR1. The material ADH0 of the curtain CUR1 may provide reflected light $LB2_k$ by reflecting and/or scattering light of the beam $LB1_k$. The light $LB2_k$ may be provided by specular reflection and/or by scattering. Scattering may cause diffuse reflection and/or diffuse refraction.

The imaging unit 100 may be arranged to form an optical image IMG1 by receiving the reflected light $LB2_k$. The imaging unit 100 may comprise imaging optics 120, which may be arranged to form an image $SD_{A,k}$ of the feature $D_{A,k}$ on an image sensor 110 by focusing reflected light $LB2_k$. The image $SD_{A,k}$ may substantially coincide e.g. with a detector pixel $DP_q$ at the time $t_0$. The image sensor 110 may convert the optical image IMG1 into a digital image FRAME0 (FIG. 8b), or into a digital image FRAME1 (FIG. 8c). The imaging optics 120 and the image sensor 110 may be selected such that the imaging unit 100 may be sensitive to the wavelength λ1 (or wavelength band) of the illuminating light LB1. The light of the illuminating light LB1 may be e.g. in the infrared range. For example, at least 90% of the optical power of the light LB1 may be at wavelengths longer than 760 nm.

The pointer feature $D_{A,k}$ may be formed by an illuminating light beam $LB1_k$. The direction of the light beam $LB1_k$ may be defined e.g. by an angle $\alpha_k$. The angle $\alpha_k$ may be e.g. an angle between the centerline of the light beam $LB1_k$ and the direction SX.

The imaging optics 120 of the imaging unit 100 may have a principal point PP1. $VLIN_k$ denotes a line defined by the principal point PP1 and the pointer feature $D_{A,k}$. The line $VLIN_k$ may be called e.g. as a line of sight. The direction of the line $VLIN_k$ may be defined e.g. by an angle $\beta_k$. The angle $\beta_k$ may be e.g. an angle between the line $VLIN_k$ and the direction SX. The angle $\beta_k$ may be determined e.g. from the position of the image $SD_{A,k}$ formed on the image sensor 110. The angle $\beta_k$ may be determined e.g. from the position of the detector pixel $DP_q$. The distance $L_k(t_0)$ between the feature $D_{A,k}$ and the principal point PP1 may be determined from the angle $\alpha_k$, from the angle $3_k$, and from the base distance $L_0$. The distance $L_k(t_0)$ between the feature $D_{A,k}$ and the principal point PP1 may be determined by triangulation from the angle $\alpha_k$, from the angle $\beta_k$, and from the base distance $L_0$.

Figure 7C:
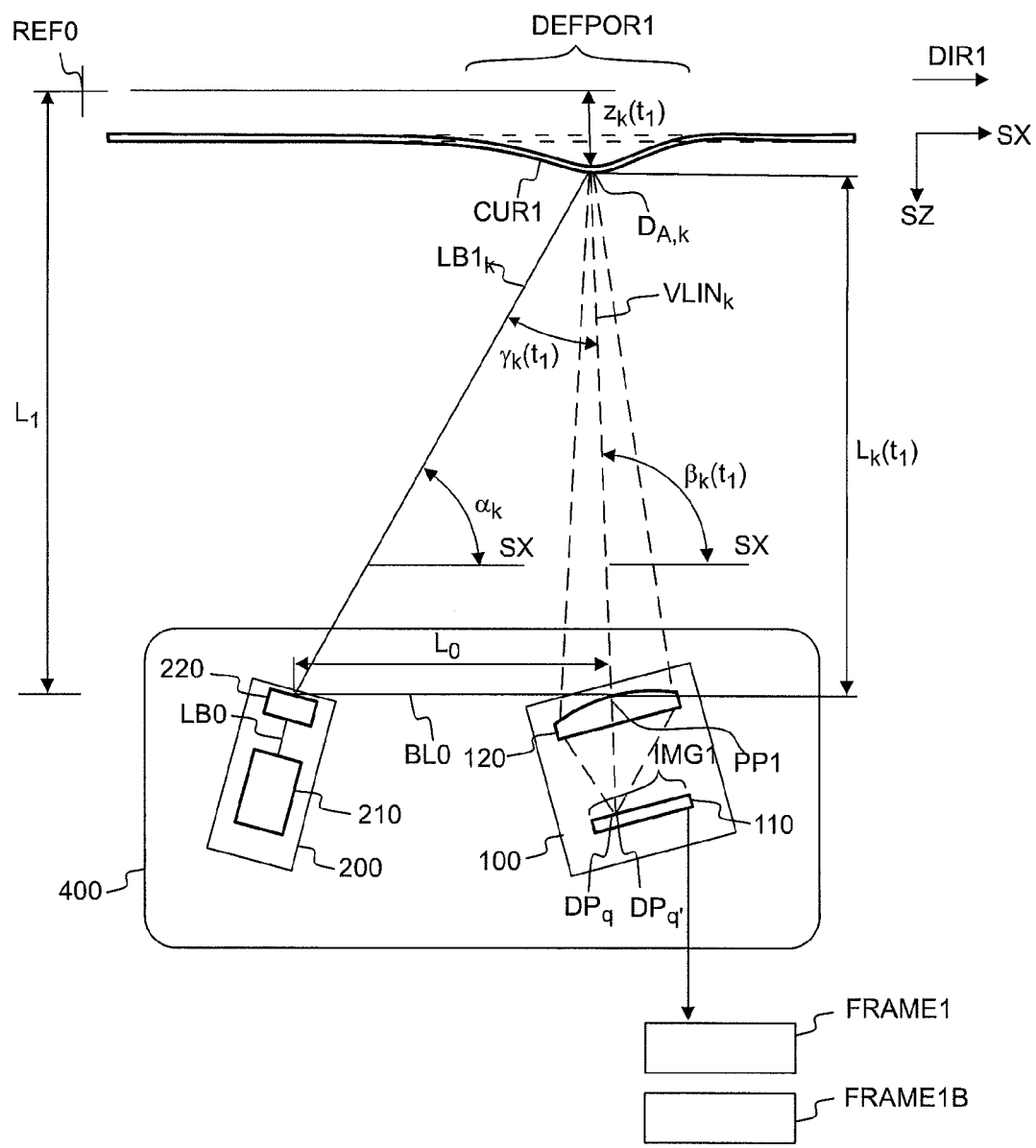
FIG. 7c shows, by way of example, in a top view, capturing an image of a projected feature in case of a deformed curtain.

Referring to FIG. 7c, a portion DEFPOR1 of the curtain CUR1 may be momentarily deformed and/or displaced at a time $t_1$. $L_k(t_1)$ may denote the distance between the principal point PP1 and the pointer feature $D_{A,k}$ at the time $t_1$. The distance $L_k(t_1)$ at the time $t_1$ may be different from the distance $L_k(t_0)$ at the time $t_0$ due to the deformation/displacement of the curtain CUR1. The position of the image $SD_{A,k}$ of the feature $D_{A,k}$ on the image sensor may depend on the distance between the principal point PP1 and the pointer feature $D_{A,k}$. The image $SD_{A,k}$ may substantially coincide e.g. with a detector pixel $DP_{q'}$ at the time $t_1$.

The coordinate $z_k(t_1,x_k,y_k)$ of the curtain CUR1 at the position of the feature $D_{A,k}$ at the time $t_1$ may be determined by triangulation from the angle $\alpha_k$, from the angle $\beta_k$, from the base distance $L_0$, and from the known position of the reference point REF0. The coordinate $z_k(t_1,x_k,y_k)$ may define the position of the curtain CUR1 in the direction SZ.

The image sensor 110 may comprise a two-dimensional array of detector pixels. The image sensor 110 may be e.g. CMOS image sensor or a CCD image sensor. The imaging unit 100 may be sensitive to infrared light LB2. The image sensor 110 of the imaging unit 100 may be e.g. a CCD sensor or a CMOS sensor. CCD is an abbreviation for charge coupled device. CMOS is an abbreviation for Complementary metal-oxide-semiconductor. The horizontal viewing sector SEC1 of the imaging unit 100 may be e.g. in the range of 30° to 60°.

The imaging unit 100 may be arranged to capture images FRAME1 at a rate, which may be e.g. in the range of 10 to 200 image frames per second, in order to provide sufficient temporal resolution. The imaging unit 100 may be arranged to capture image images FRAME1 at a rate, which may be e.g. in the range of 20 to 40 frames per second.

Pixel values of the image FRAME1 may be quantized e.g. by a local thresholding operation to provide a binary image. The value of each pixel of the binary image may be either 0 or 1. The binary image may be subsequently analyzed at a high rate by a data processor e.g. for determining the identity for each sub-image $SG_k$, and/or for neighbor extraction.

The monitoring unit 400 may be arranged to provide distance information. The distance information may comprise e.g. one or more distance values $L_k(t_1)$ and/or one or more coordinate values $z_k(t_1,x_k,y_k)$. The distance $L_k(t_1)$ or depth information $z_k(t_1,x_k,y_k)$ may be determined at a resolution, which may be e.g. in the range of 0.1 mm to 0.5 mm, 0.5 mm to 1 mm, 1 mm to 2 mm, or 2 mm to 4 mm. The resolution may depend on the distance between the curtain CUR1 and the principal point PP1, and on the length $L_0$ of the baseline BL0. The resolution may depend on the angle $\gamma_k$ between the direction of an illuminating light beam $LB1_k$ and a line of sight $VLIN_k$. The distance $L_{NORM}$ between the curtain CUR1 and the principal point PP1 may be e.g. in the range of 0.5 to 4 m. In particular, the distance between the curtain CUR1 and the principal point PP1 may be e.g. in the range of 1.0 to 4.0 m in order to minimize the risk of contaminating the optics with the coating material and/or in order to provide space for maintenance operations. The distance $L_{NORM}$ may be e.g. in the range of 0.5 m to 3.0 m. The distance $L_{NORM}$ may be e.g. in the range of 1.5 m to 3.0 m. The length of the baseline BL0 may be e.g. greater than or equal to 10 mm in order to provide sufficient resolution for measuring the distance $L_k(t_1)$. The angle $\gamma_k$ may be e.g. greater than or equal to 0.2 degrees in order to provide sufficient resolution for measuring the distance $L_k(t_1)$.

The image FRAME1 may be slightly blurred e.g. due to defocusing and/or optical aberrations. In an embodiment, the size of the pointer features may be rather large in order to facilitate reliable detection of the pointer features by using the imaging unit 100. For example, the smallest dimension (e.g. height, width or diameter) of the pointer features $D_{A,k}$ may be e.g. greater than 0.001 times the width $w_e$ of the curtain CUR1.

The image sensor 110 may be arranged to provide a further image frame FRAME1B at a time $t_3$. The further image frame FRAME1B may be utilized e.g. for measuring distance information at the time $t_3$. In particular, the further image frame FRAME1B may be utilized e.g. for detecting the presence of a foreign object O1 (FIG. 8d).

Figure 7D:
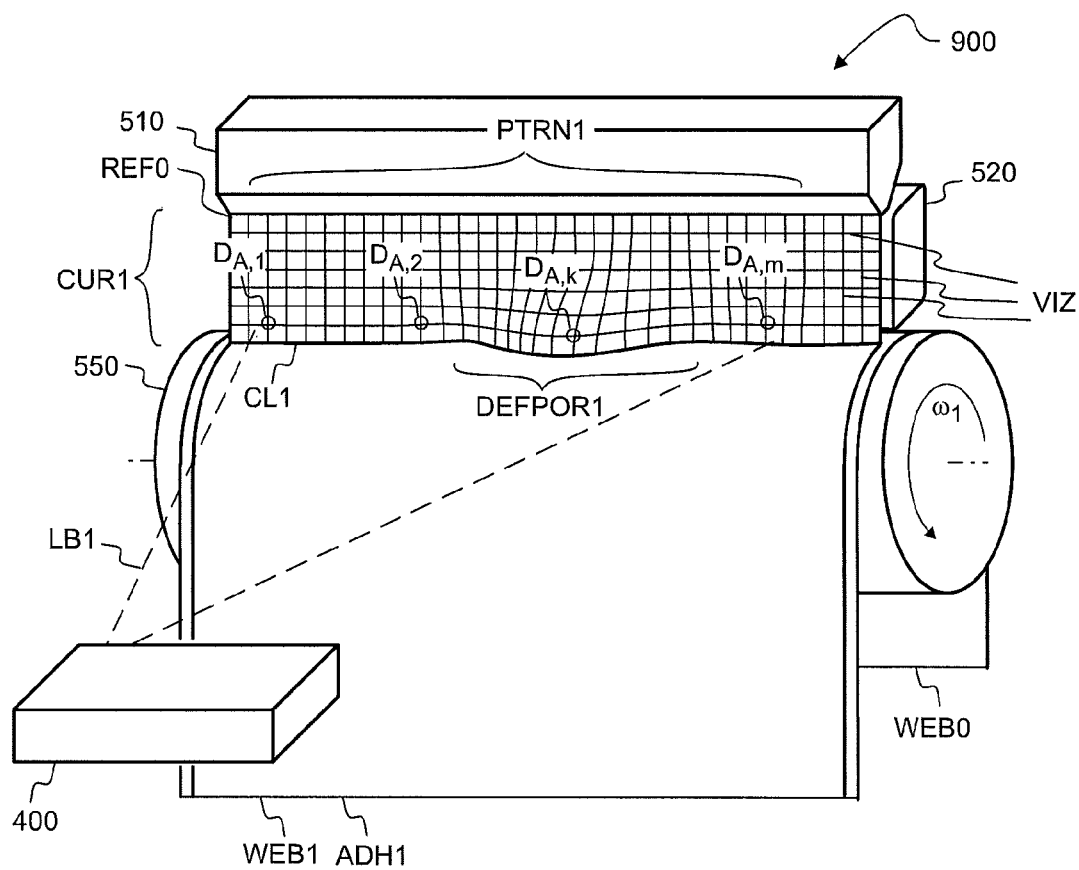
FIG. 7d shows, by way of example, in a three dimensional view, a deformed curtain.

FIG. 7d shows projecting the primary pattern PTRN1 on the curtain CUR1. The primary pattern PTRN1 may comprise pointer features $D_{A,1}$, $D_{A,2}$, $D_{A,k}$, $D_{A,m}$. The curtain CUR1 may have a deformed portion DEFPOR1. The three-dimensional shape of the curtain CUR1 has been visualized in this example by an imaginary mesh pattern VIZ. It should be understood that the pattern PTRN1 does not need to comprise the mesh pattern VIZ.

Figure 8A:
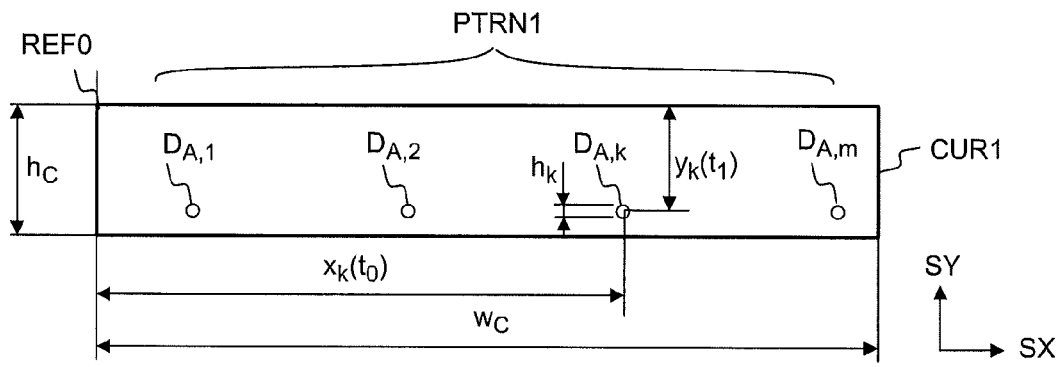
FIG. 8a shows, by way of example, in a side view, a plurality of features projected on the curtain.

FIG. 8a shows a plurality of pointer features $D_{A,1}$, $D_{A,2}$, $D_{A,k}$, $D_{A,m}$ projected on the curtain CUR1. The pointer feature $D_{A,k}$ may have a dimension $h_k$. The dimension $h_k$ may be e.g. the height or a diameter of a dot.

Figure 8B:
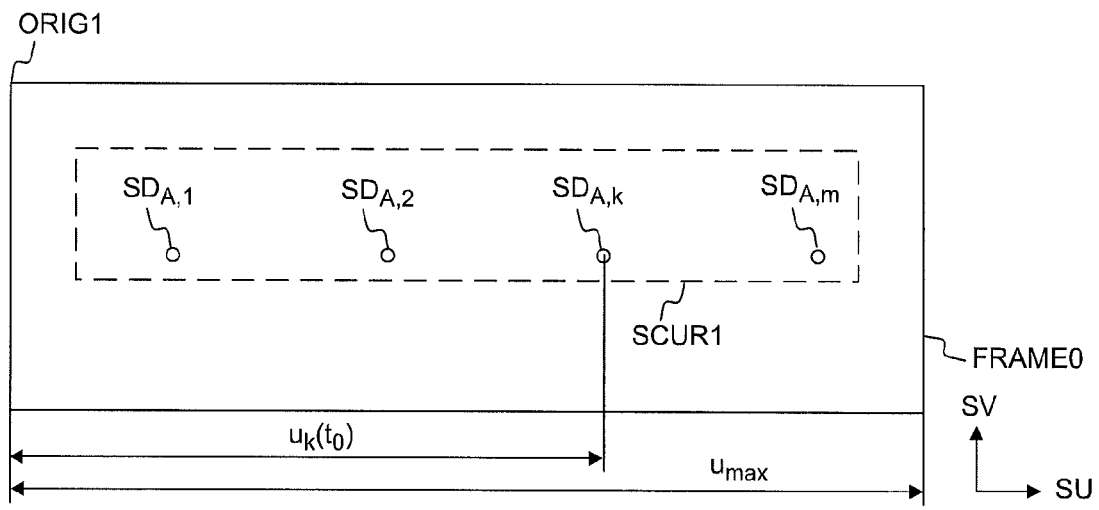
FIG. 8b shows, by way of example, an image of the features projected on the curtain in the reference state.
Figure 8C:
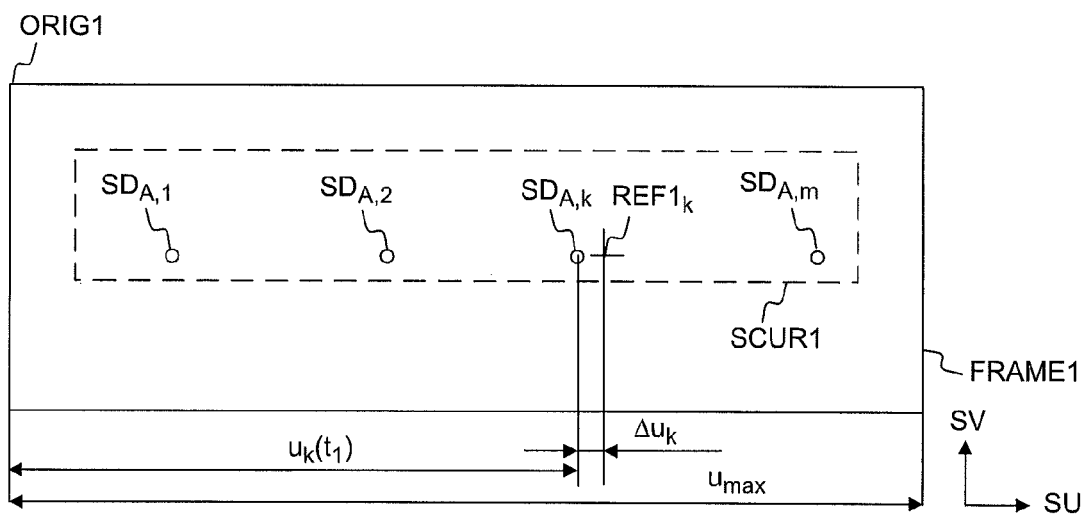
FIG. 8c shows, by way of example, an image of the features projected on the curtain in case of a deformed curtain.
Figure 8D:
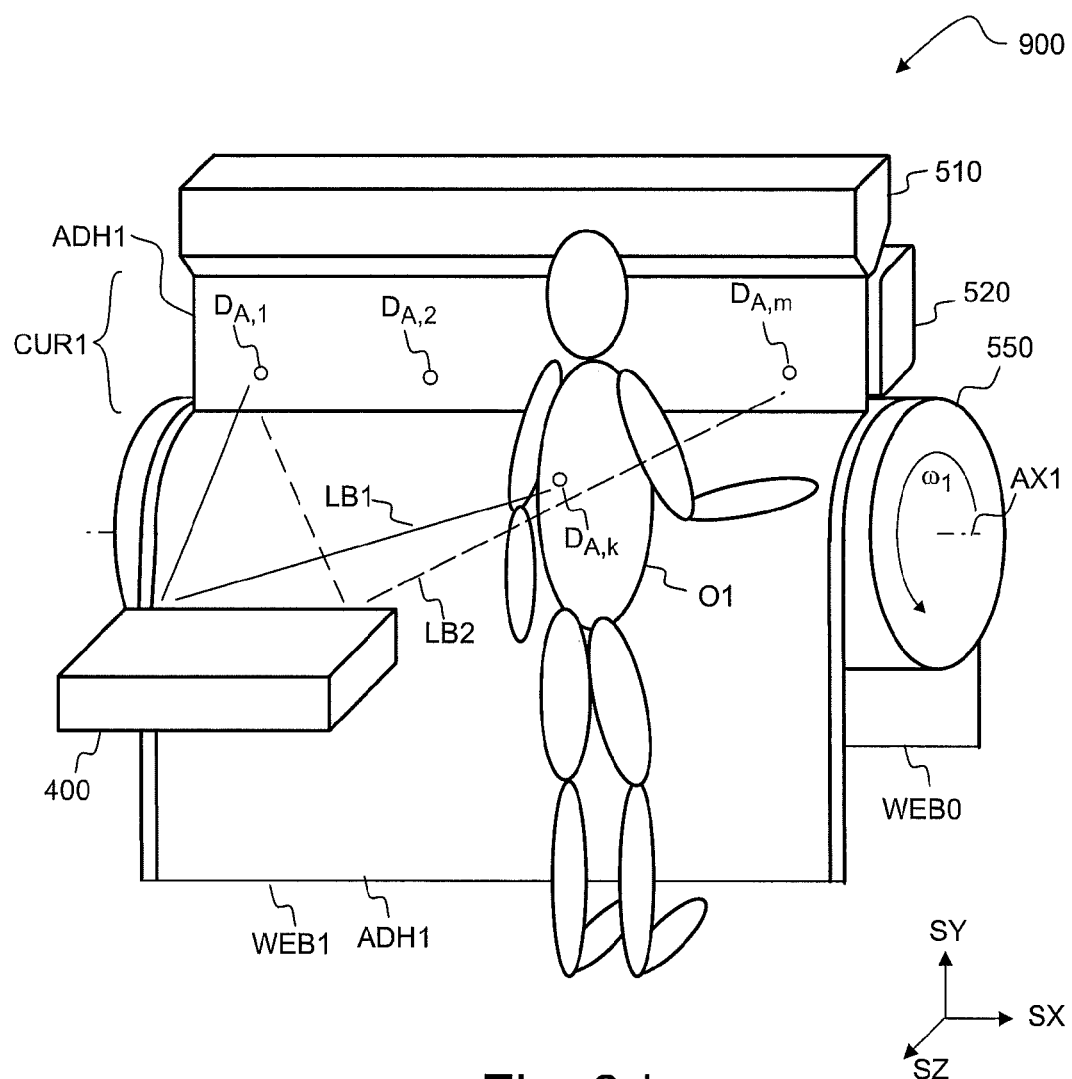
FIG. 8d shows, by way of example, in a three dimensional view, a foreign object positioned between the monitoring unit and the curtain.

FIG. 8b shows a digital image FRAME1, which comprises images $SD_{A,1}$, $SD_{A,2}$, $SD_{A,k}$, $SD_{A,m}$ of the pointer features $D_{A,1}$, $D_{A,2}$, $D_{A,k}$, $D_{A,m}$. The image $SD_{A,k}$ may be an image of the pointer feature $D_{A,k}$. The digital image FRAME1 may optionally comprise an image SCUR1 of the curtain CUR1, but this is not necessary. The images $SD_{A,1}$, $SD_{A,2}$, $SD_{A,k}$, $SD_{A,m}$, SCUR1 may be called as sub-images. The digital image FRAME0 may represent the situation at a time $t_0$. $u_k(t_0)$ denotes a position coordinate of the sub-image $SD_{A,k}$ in the image FRAME0. The position $u_k(t_0)$ of the sub-image $SD_{A,k}$ representing the time $t_0$ may be determined by analyzing the digital image FRAME0. The angle $\beta_k(t_0)$ shown in FIG. 7b may be determined from the position of the sub-image $SD_{A,k}$, by analyzing the digital image FRAME0. $u_{max}$ may denote the total width of the digital image FRAME0.

FIG. 8c shows a digital image FRAME1, which comprises the sub-images $SD_{A,1}$, $SD_{A,2}$, $SD_{A,k}$, $SD_{A,m}$ representing the time $t_1$, i.e. when the curtain CUR1 was displaced and/or deformed. $u_k(t_1)$ denotes a position of the sub-image $SD_{A,k}$ in the image FRAME1 which was captured at the coating time $t_1$.

The position $u_k(t_1)$ of the sub-image $SD_{A,k}$ representing the time $t_1$ may be determined by analyzing the digital image FRAME1. The angle $\beta_k(t_1)$ shown in FIG. 7c may be determined from the position of the sub-image $SD_{A,k}$, by analyzing the digital image FRAME1. $u_{max}$ may denote the total width of the digital image FRAME1.

$REF1_k$ denotes the position of the sub-image $SD_{A,k}$ in the reference image FRAME0, i.e. at the coating time $t_0$. $\Delta u_k$ denotes a displacement between the position of the sub-image $SD_{A,k}$ at the time $t_1$ and the position of the sub-image $SD_{A,k}$ at the time $t_0$.

The position of a predetermined portion of the curtain CUR1 may be monitored by:
projecting one or more pointer features $D_{A,1}$, $D_{A,2}$, $D_{A,k}$, $D_{A,m}$ on the curtain CUR1,
capturing a digital image FRAME1 which comprises a sub-image $SD_{A,k}$ of a pointer feature $D_{A,k}$, and
determining the position of the pointer feature $D_{A,k}$ from the position of the sub-image $SD_{A,k}$ by triangulation.

The position of a predetermined portion of the curtain CUR1 may be measured by:
projecting one or more pointer features $D_{A,1}$, $D_{A,2}$, $D_{A,k}$, $D_{A,m}$ on the curtain CUR1,
capturing a digital image FRAME1, which comprises a sub-image $SD_{A,k}$ of a pointer feature $D_{A,k}$, and
determining the position of the pointer feature $D_{A,k}$ from the position of the sub-image $SD_{A,k}$ by triangulation.

The deformation and/or displacement of the curtain may be measured by:
projecting one or more pointer features $D_{A,1}$, $D_{A,2}$, $D_{A,k}$, $D_{A,m}$ on the curtain CUR1,
capturing a digital image FRAME1, which comprises a sub-image $SD_{A,k}$ of a pointer feature $D_{A,k}$, and
determining the position of the pointer feature $D_{A,k}$ from the position of the sub-image $SD_{A,k}$ by triangulation, and
comparing the determined position $z(t_1)$ of the pointer feature $D_{A,k}$ with a reference position $z(t_0)$.

The reference image FRAME0 may be captured e.g. by the imaging unit 100. In an embodiment, the reference image FRAME0 may also be provided by a computer simulation from a numerically defined reference shape of the curtain CUR1. The reference shape of the curtain CUR1 may be e.g. planar or curved. The reference image FRAME0 may be provided without using an imaging unit. The reference position $REF1_k$ may be provided by computer simulation without using an imaging unit.

Referring to FIG. 8d, the field of view of the monitoring unit 400 may be temporarily obstructed by an object O1, which is different from the curtain CUR1. The object may be called e.g. as a foreign object. In particular, the object O1 may be a component of the apparatus 900, a human operator of the apparatus 900, or an object held by a human operator (e.g. a tool).

The position of a pointer feature $D_{A,k}$ projected on the surface of the foreign object O1 may substantially deviate from the position of said feature $D_{A,k}$ in the reference situation. Consequently, it may be difficult to determine which one of several sub-images appearing in the digital image FRAME1 is the sub-image of the feature $D_{A,k}$. The displacement of the sub-image $SD_{A,k}$ of said pointer feature $D_{A,k}$ may so large that it may be difficult to determine the identity of the corresponding feature $D_{A,k}$.

Figure 9A:
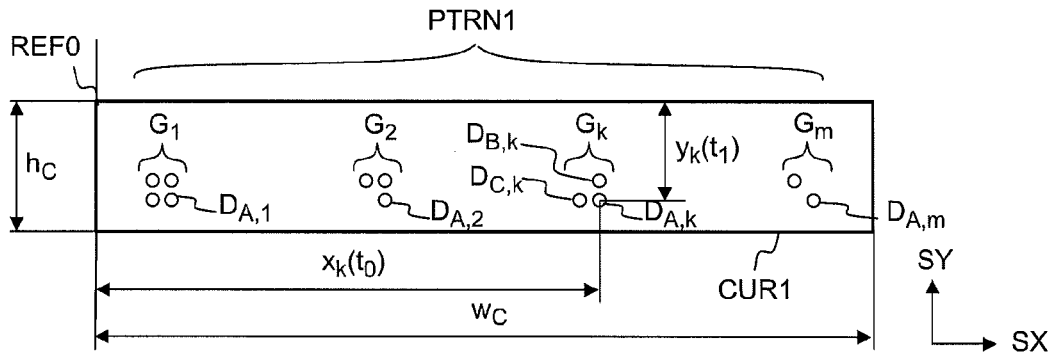
FIG. 9a shows, by way of example, in a side view, several sub-patterns projected on the curtain.

Referring to FIG. 9a, the projecting unit 200 may be arranged to project a pattern PTRN1 on the curtain, wherein the pattern may simultaneously comprise two or more dissimilar sub-patterns $G_1$, $G_2$, $G_k$, $G_m$. FIG. 9a shows, in a side view, the curtain CUR1 and a plurality of sub-patterns $G_1$, $G_2$, $G_k$, $G_m$, which have different shapes. For example, each sub-pattern may comprise e.g. two or more spots having characteristic positions and/or distances with respect to each other. A first sub-pattern $G_k$ may be located between a second sub-pattern $G_2$ and a third sub-pattern $G_m$, wherein the shape of the first sub-pattern $G_k$ may be different from the shape of the second sub-pattern $G_2$ and different from the shape of the third sub-pattern $G_m$. Thus, the identity (k) of the first sub-pattern $G_k$ may be determined by analyzing the shape of the sub-image $SG_k$ of the first sub-pattern $G_k$. The identity (k) of the first sub-pattern $G_k$ may be determined by determining whether the shape of the sub-image $SG_k$ of the first sub-pattern $G_k$ matches with the shape of a reference image.

The identity of each sub-pattern $G_1$, $G_2$, $G_k$, $G_m$ may be determined based on the characteristic shape of the sub-pattern $G_1$, $G_2$, $G_k$, $G_m$. The sub-pattern $G_1$ may comprise a feature $D_{A,1}$, the sub-pattern $G_2$ may comprise a feature $D_{A,2}$, the sub-pattern $G_k$ may comprise features $D_{A,k}$, $D_{B,k}$, $D_{C,k}$ and the sub-pattern $G_m$ may comprise a feature $D_{A,m}$. The pointer features $D_{A,1}$, $D_{A,2}$, $D_{A,k}$, $D_{A,m}$ may be substantially similar, but each pointer feature $D_{A,1}$, $D_{A,2}$, $D_{A,k}$, $D_{A,m}$ may still be associated with a different identity because they belong to sub-patterns, which have different shapes.

The identity of each sub-pattern $G_1$, $G_2$, $G_k$, $G_m$ may be determined by comparing the shape of each sub-pattern with reference images. For example, when the sub-pattern $G_k$ matches with a reference image associated with an identifier k, said sub-pattern $G_k$ may also be associated with said identifier k.

Figure 9B:
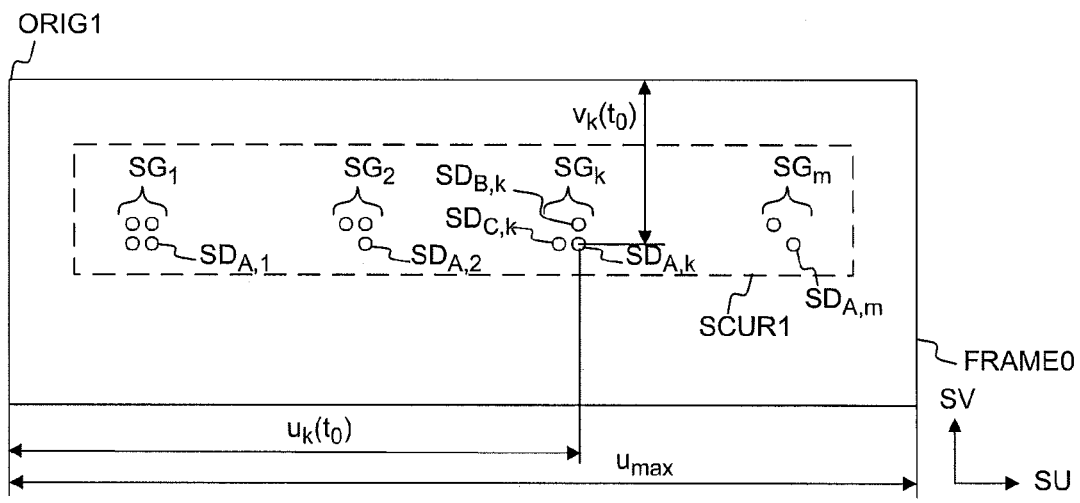
FIG. 9b shows, by way of example, an image of the sub-patterns projected on the curtain in the reference situation.

Referring to FIG. 9b, a digital reference image FRAME0 may comprise an image of a pattern PTRN1 projected on the curtain CUR1 when the curtain CUR1 was in a reference state. The digital image FRAME0 may comprise a plurality of sub-images of the sub-patterns. The digital image FRAME0 may comprise a sub-image $SG_1$ of the sub-pattern $G_1$, a sub-image $SG_2$ of the sub-pattern $G_2$, a sub-image $SG_k$ of the sub-pattern $G_k$, and a sub-image $SG_m$ of the sub-pattern $G_m$. The sub-image $SG_k$ may comprise sub-images $SD_{A,k}$, $SD_{B,k}$, $SD_{C,k}$, which may be images of the features $D_{A,k}$, $D_{B,k}$, $D_{B,k}$ of the sub-pattern $G_k$. The digital image FRAME0 may represent the situation at a time $t_0$. The digital image FRAME0 may represent the curtain CUR1 when it is in reference state. The reference image FRAME0 may comprise a plurality of reference sub-images of the sub-patterns when the curtain CUR1 is in reference state.

Figure 9C:
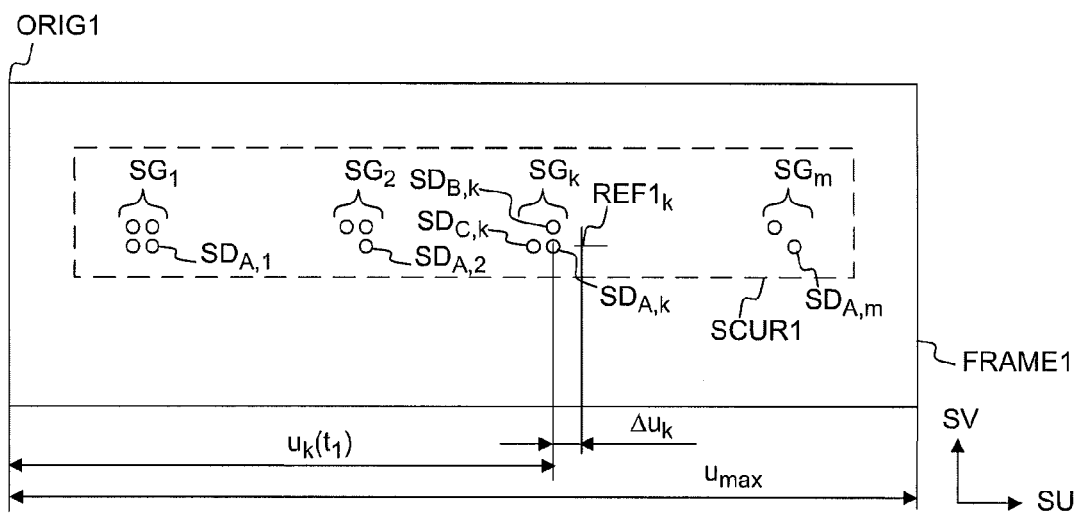
FIG. 9c shows, by way of example, an image of the sub-patterns projected on the curtain in case of a deformed curtain.

Referring to FIG. 9c, a digital image FRAME1 may comprise an image of a pattern projected on the curtain CUR1 when the curtain CUR1 is deformed and/or displaced and/or when a sub-pattern is projected on a foreign object O1. The sub-image $SG_k$ may be an image of an unknown sub-pattern. The sub-image $SG_k$ may be an image of a sub-pattern, which may be temporarily unknown until it is identified. The identity of the unknown sub-pattern of FIG. 9c may be determined by comparing the unknown sub-image $SG_k$ of FIG. 9c with one or more known sub-images of the digital reference image FRAME0. The unknown sub-pattern may be determined to be associated with an identifier (k) when the sub-image of the digital image FRAME1 is detected to match with a reference sub-image $SG_k$ associated with said identifier (k).

The method may comprise:
  projecting one or more features sub-patterns $G_1$, $G_2$, $G_k$, $G_m$ on the curtain CUR1,
  capturing a digital image FRAME1 which comprises a first sub-image of a projected sub-pattern,
  determining an identity for the first sub-image by determining whether the first sub-image substantially matches with a sub-image $SG_k$ of a sub-pattern $G_k$, which has known identity (k), and
  determining the position of the projected sub-pattern from the position of the first sub-image by triangulation.

Figure 9D:
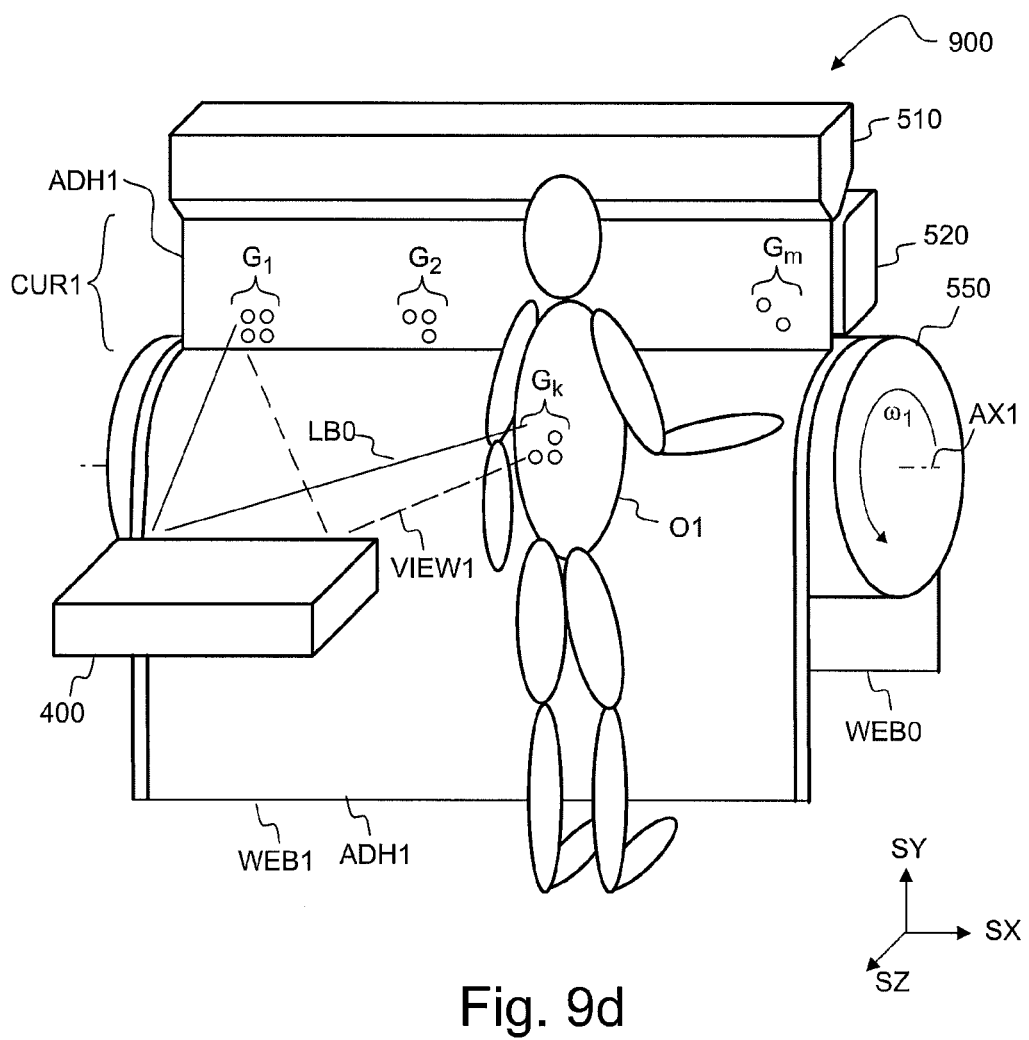
FIG. 9d shows, by way of example, in a three dimensional view, a foreign object positioned between the monitoring unit and the curtain.

Referring to FIG. 9d, the identity of several sub-patterns $G_1$, $G_2$, $G_k$, $G_m$ may be determined also in a situation where one or more of the sub-patterns $G_1$, $G_2$, $G_k$, $G_m$ are projected on the surface of a foreign object O1. For example, a sub-pattern $G_k$ projected on the surface of the object O1 may be recognized by determining whether an unknown sub-image of the image FRAME2 matches with the sub-image $SG_k$ of the reference image FRAME0.

Figure 10A:
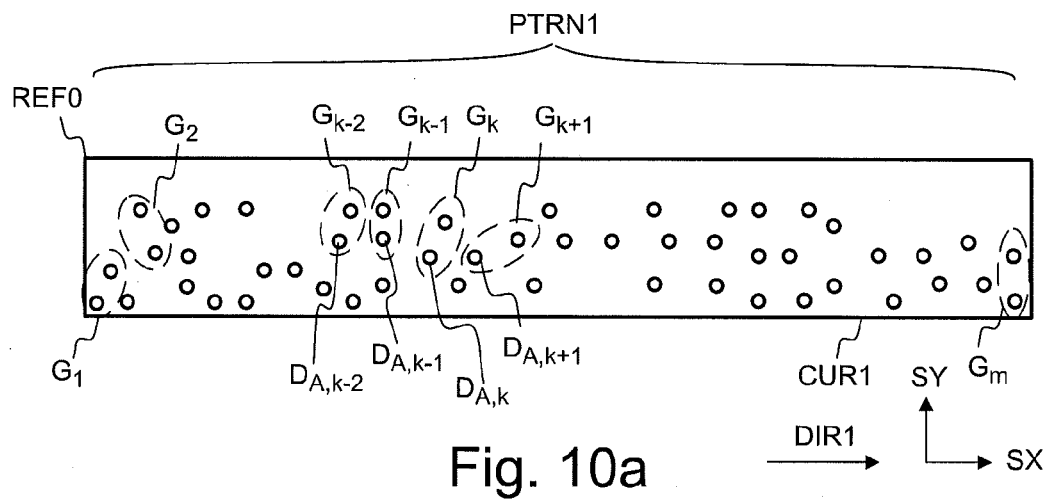
FIG. 10a shows, by way of example, in a side view, a pattern projected on the curtain.

Referring to FIG. 10a, the projecting unit 200 may be arranged to project a pattern PTRN1 on the curtain CUR1, wherein the projected pattern PTRN1 may comprise a plurality of sub-patterns $G_1$, $G_2$, . . . , $G_{k-2}$, $G_{k-1}$, $G_k$, $G_{k+1}$, . . . $G_m$. The pattern PTRN1 may comprise e.g. a plurality of spatially separate pointer features, which may be located e.g. in pseudo random positions. Each sub-pattern $G_1$, . . . , $G_{k-2}$, $G_{k-1}$, $G_k$, $G_{k+1}$, . . . $G_m$. may comprise e.g. two or more pointer features. Each sub-pattern may be formed of e.g. 3, 4, 5, or 6 dots. Each sub-pattern may be formed of six dots. The reliability of identification may be increased by using a high number of pointer features within a single sub-pattern. On the other hand, data processing speed and/or spatial resolution may be improved by using a small number of pointer features within a single sub-pattern The pattern PTRN1 may be projected on the curtain CUR1 e.g. by using a combination of a laser beam LB0 and a holographic element 220.

The pattern PTRN1 may be e.g. a speckle pattern generated by diffracting laser light LB0. Each sub-pattern $G_1$, $G_2$, . . . , $G_{k-2}$, $G_{k-1}$, $G_k$, $G_{k+1}$, . . . $G_m$ may comprise e.g. two or more spots. A first sub-pattern $G_k$ may comprise two or more spots, the number of spots of the second sub-pattern $G_{k-1}$ may be greater than or equal to the number of spots of the first sub-pattern $G_k$, and the number of spots of the third sub-pattern $G_{k+1}$ may be greater than or equal to the number of spots of the first sub-pattern $G_k$. The first sub-pattern $G_k$ may be located between the second sub-pattern $G_{k-1}$ and the third sub-pattern $G_{k+1}$.

When the distance $L_k$ between a predetermined sub-pattern $G_k$ and the imaging unit 100 is increased, the sub-image $SG_k$ in the digital image FRAME1 may be displaced and enlarged, when compared with the sub-image $SG_k$ in the reference image FRAME0. When the distance $L_k$ between a predetermined sub-pattern $G_k$ and the imaging unit 100 is decreased, the sub-image $SG_k$ in the digital image FRAME1 may be displaced and shrunk, when compared with the sub-image $SG_k$ in the reference image FRAME0. Thus, a digital image FRAME1 may comprise a first sub-image $SG_k$ of a sub-pattern $G_k$, and the reference image FRAME0 may comprise a second sub-image $SG_k$ of said sub-pattern $G_k$ such that the first sub-image $SG_k$ is displaced and scaled when compared with the second sub-image $SG_k$. The reference position $REF1_k$ may indicate the position of said second sub-image $SG_k$. The distance $L_k$ may sometimes vary so much that the first sub-image $SG_k$ is displaced so that a third sub-image $SG_{k+1}$ of the digital image FRAME1 is located between the first sub-image $SG_k$ and the reference position $REF1_k$. The third sub-image $SG_{k+1}$ may be a sub-image of a second sub-pattern $G_{k+1}$. In that case, it may be difficult to associate a detected sub-image with the corresponding reference position.

For facilitating said association, the first sub-pattern $G_k$ may be locally unique such that it does not match with any other sub-pattern in the vicinity of the first sub-pattern $G_k$. In an embodiment, the first sub-pattern $G_k$ may be globally unique such that it does not match with any other sub-pattern of the pattern PTRN1.

The distance $L_k$ may be determined from the displacement $\Delta u_k$ by triangulation. The monitoring unit 400 may be arranged to associate a detected sub-image $SG_k$ with a corresponding reference position $REF1_k$, in order to determine the displacement $\Delta u_k$. However, associating a detected sub-image $SG_k$ with the corresponding reference position $REF1_k$ may be difficult e.g. when the sub-image $SG_k$ is displaced so that another sub-image $SG_{k+1}$ or $SG_{k-1}$ is located between the sub-image $SG_k$ and the reference position $REF1_k$.

In an embodiment, a detected sub-image $SG_k$ may be associated with the corresponding reference position $REF1_k$ based on the shape of the detected sub-image $SG_k$. The detected sub-image $SG_k$ may be identified based on the shape of the detected image $SG_k$, and the corresponding reference position $REF1_k$ may be determined based on the identity of the detected image $SG_k$. In an embodiment, the sub-pattern $G_k$ may have a distinct shape so that the sub-image $SG_k$ of the sub-pattern $G_k$ may be identified based on the shape of the sub-pattern $G_k$. In an embodiment, each sub-pattern $G_k$ may represent an identifying code.

In an embodiment, the sub-image $SG_k$ may be unique so that the sub-image $SG_k$ may be reliably and unambiguously associated with the correct reference position $REF1_k$ based on the shape of the sub-image $SG_k$. In an embodiment, each sub-pattern $G_{k-1}$, $G_k$, $G_{k+1}$ may have a unique shape. In an embodiment, the sub-pattern $G_k$ may be located between the sub-patterns $G_{k-1}$, $G_{k+1}$, wherein the shape of the sub-pattern $G_k$ may be different from the shape of the sub-pattern $G_{k-1}$, and the shape of the sub-pattern $G_k$ may be different from the shape of the sub-pattern $G_{k+1}$.

The monitoring unit 400 may be arranged to detect that a digital image FRAME1 comprises one or more sub-images $SG_k$, $SG_{k+1}$. A digital image FRAME1 may comprise one or more detected sub-images $SG_k$, $SG_{k+1}$. The monitoring system may be arranged to determine an identity (k) of a detected sub-image $SG_k$. The monitoring unit 400 may be arranged to determine the identity of a detected sub-image $SG_k$ by comparing the detected sub-image $SG_k$ with one or more candidate sub-images $SG_{k-1}$, $SG_k$, $SG_{k+1}$. The monitoring unit 400 may be arranged to determine the identity of a detected sub-image $SG_k$ by comparing the shape of the detected sub-image $SG_k$ with the shapes of one or more candidate sub-images $SG_{k-1}$, $SG_k$, $SG_{k+1}$. In an embodiment, each sub-pattern $G_k$, $G_{k+1}$ may have a unique shape such that the identity of the sub-image of each sub-pattern $G_k$, $G_{k+1}$ may be determined based on the shape of sub-image.

The monitoring unit 400 may be arranged to determine a reference position $REF1_k$ corresponding to the detected sub-image $SG_k$ based on the identity of the detected sub-image $SG_k$. The monitoring unit 400 may be arranged to determine a reference position $REF1_k$ of the detected sub-image $SG_k$ based on the identity of the detected sub-image $SG_k$.

For example, a plurality of identifiers ( . . . , k−1, k, k+1 . . . ) and a plurality of reference positions $REF1_{k-1}$, $REF1_k$, $REF1_{k+1}$ may be contained in table such that each identifier is associated with a different reference position.

In an embodiment, each sub-pattern may be a group of spots that may be unique within the whole pattern PTRN1 and can therefore be used to uniquely determine the location in the pattern PTRN1.

Figure 10B:
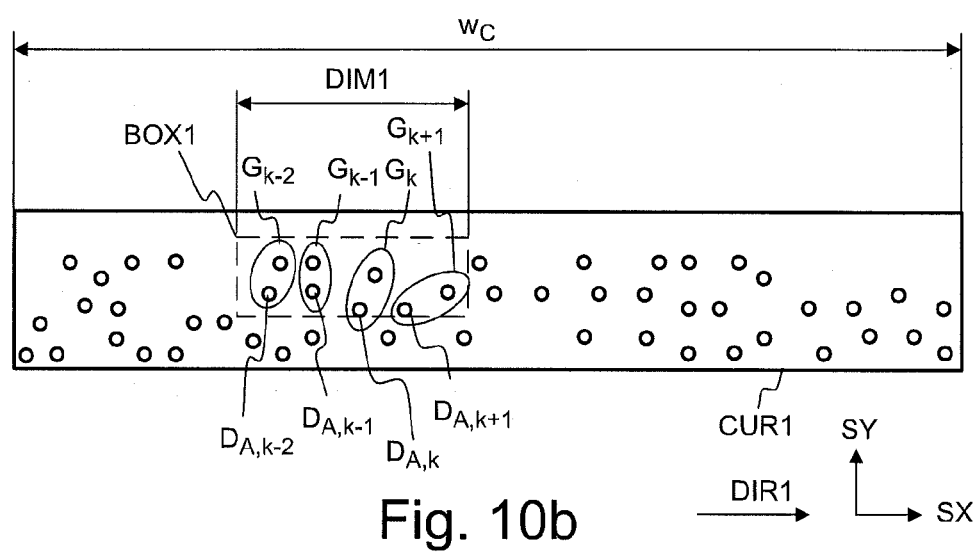
FIG. 10b shows, by way of example, in a side view, a pattern projected on the curtain.

Referring to FIG. 10*b*, a given sub-pattern $G_k$ does not need to be unique within the whole area of the pattern PTRN1. It may be sufficient when the sub-pattern $G_k$ is locally unique. It may be sufficient if the sub-pattern $G_k$ is unique within a portion BOX1 of the pattern PTRN1. The portion BOX1 may be called e.g. as a search portion BOX1. The pattern PTRN1 may optionally comprise other sub-patterns which are identical to the sub-patterns $G_k$, as long as the other identical sub-patterns $G_k$ are located outside the search portion BOX1. The dimensions DIM1, DIM2 of the search portion BOX1 may be selected such that the identity of the sub-pattern $G_k$ contained in the search portion BOX1 may be determined with sufficient reliability even when pattern PTRN1 comprises other identical sub-patterns outside the search portion BOX1.

The search portion BOX1 may comprise e.g. sub-patterns $G_{k-2}$, $G_{k-1}$, $G_k$, $G_{k+1}$. The sub-pattern $G_k$ may have a characteristic shape in order to allow determining the correct reference position $REF1_k$ with a sufficient reliability. The sub-pattern $G_k$ may be different from all other sub-patterns of the search portion BOX1 such that the sub-pattern $G_k$ cannot be transformed into any other sub-pattern (e.g. $G_{k-2}$, $G_{k-1}$, or $G_{k+1}$) of the portion BOX1 only by using a linear translation operation in the direction DIR1 and a scaling operation. The direction DIR is parallel to the baseline BL0 of the monitoring unit 400. The sub-pattern $G_k$ may be different from all other sub-patterns of the search portion BOX1 such that the sub-pattern $G_k$ cannot be transformed into any other sub-pattern (e.g. $G_{k-2}$, $G_{k-1}$, or $G_{k+1}$) of the portion BOX1 without using a rotation operation. The sub-pattern $G_k$ may be different from all other sub-patterns of the search portion BOX1 such that the sub-pattern $G_k$ cannot be transformed into any other sub-pattern (e.g. $G_{k-2}$, $G_{k-1}$, or $G_{k+1}$) of the portion BOX1 by a linear translation operation in the direction DIR1 without using a rotation operation.

In an embodiment, a first sub-pattern $G_k$ of the search portion does not match with any of the other sub-patterns $G_{k-2}$, $G_{k-1}$, $G_{k+1}$ within said search portion BOX1. Each sub-pattern within the search portion BOX1 may be unique within the search portion BOX1 and can therefore be used to uniquely determine a location within the search portion BOX1. The sub-pattern $G_{k-2}$ may comprise spots $D_{A,k-2}$, $D_{B,k-2}$. The sub-pattern $G_{k-1}$ may comprise spots $D_{A,k-1}$, $D_{B,k-1}$. The sub-pattern $G_k$ may comprise spots $D_{A,k}$, $D_{B,k}$. The sub-pattern $G_{k+1}$ may comprise spots $D_{A,k+1}$, $D_{B,k+1}$.

Figure 10C:
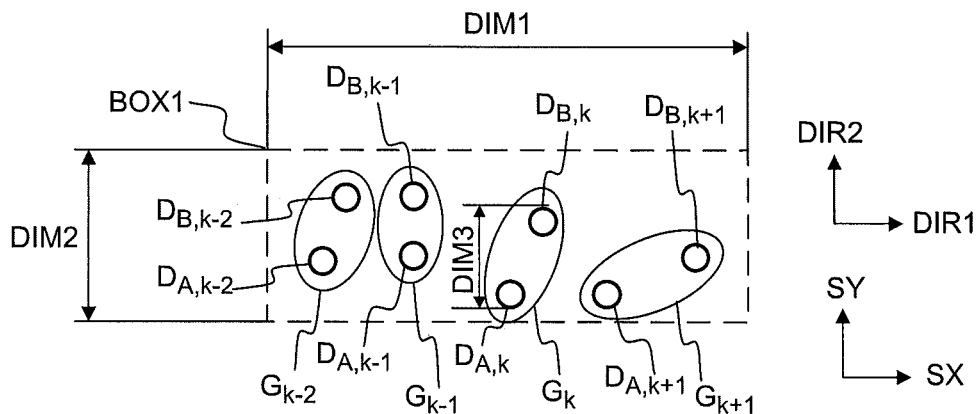
FIG. 10c shows, by way of example, in a side view, a search portion, which contains several sub-patterns.

Referring to FIG. 10*c*, the direction DIR1 denotes a direction defined by the baseline BL0 of the monitoring unit 400, and the direction DIR2 is perpendicular to the direction DIR1. The search portion BOX1 may have a dimension DIM1 in the direction DIR1, and the search portion BOX1 may have a dimension DIM2 in the direction DIR2. The sub-pattern $G_k$ may have a dimension DIM3 in the direction DIR2. The dimension DIM1 of the search portion BOX1 may be selected e.g. based on the expected range of distances which need to be measured by the monitoring unit 400. For example, the dimension DIM1 may be e.g. in the range of 10% to 40% of the width $w_C$ of the curtain CUR1. The dimension DIM2 of the search portion BOX1 may be e.g. in the range of 100% to 200% of the dimension DIM3. The direction DIR1 may be substantially parallel to the direction SX e.g. when the baseline BL0 of the monitoring unit 400 is horizontal. The DIR1 may be substantially parallel to the direction SY e.g. when the baseline BL0 of the monitoring unit 400 is vertical.

Figure 10D:
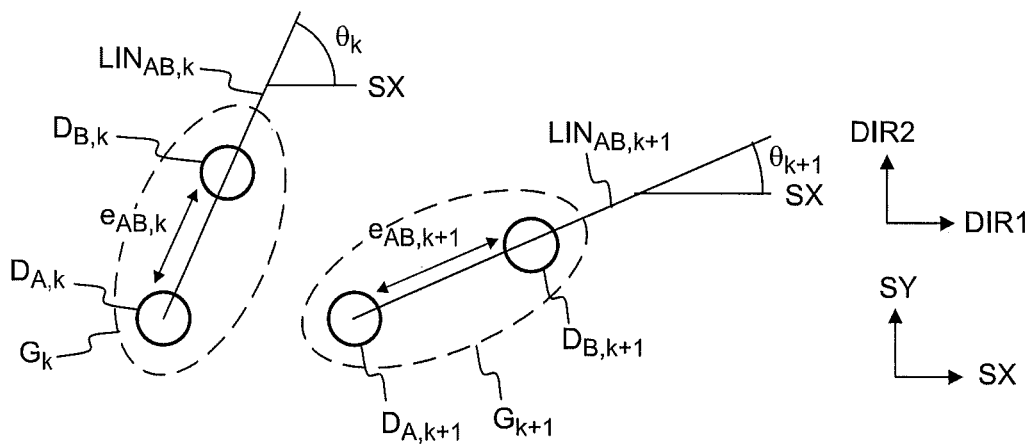
FIG. 10d shows, by way of example, in a side view, a search portion, which contains several sub-patterns.

Referring to FIG. 10*d*, a sub-pattern $G_k$ may comprise spots $D_{A,k}$, $D_{B,k}$, and a sub-pattern $G_{k+1}$ may comprise spots $D_{A,k+1}$, $D_{B,k+1}$. The spots $D_{A,k}$, $D_{B,k}$ may define a line $LIN_{AB,k}$, and the spots $D_{A,k+1}$, $D_{B,k+1}$ may define a line $LIN_{AB,k+1}$. The direction of the $LIN_{AB,k}$ may be defined by an angle $\theta_k$ with respect to a reference direction, e.g. with respect to the direction SX. The direction of the $LIN_{AB,k+1}$ may be defined by an angle $\theta_{k+1}$ with respect to a reference direction, e.g. with respect to the direction SX. The position of the spot $D_{B,k}$ may be defined by the angle $\theta_k$ and by a distance $e_{AB,k}$ with respect to the spot $D_{A,k}$. The position of the spot $D_{B,k+1}$ may be defined by the angle $\theta_{k+1}$ and by a distance $e_{AB,k+1}$ with respect to the spot $D_{A,k+1}$. The angle $\theta_{k+1}$ may be substantially different from the angle $\theta_k$ such that the sub-pattern $G_k$ cannot be transformed into the sub-pattern $G_{k+1}$ without performing a rotation operation.

Figure 10E:
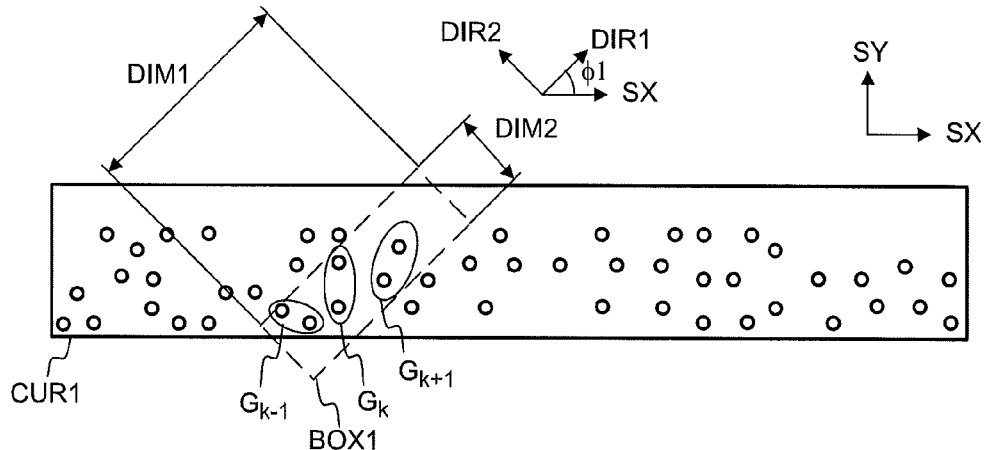
FIG. 10e shows, by way of example, in a side view, a first sub-pattern and a second sub-pattern.

Referring to FIG. 10*e*, the baseline BL0 of the monitoring unit 400 may have an arbitrary orientation with respect to the curtain CUR1. The orientation of the direction DIR1 of the baseline BL0 may be defined e.g. by an angle $\phi 1$ with respect to a reference direction. The reference direction may be e.g. the direction SX. The direction DIR1 may be substantially parallel to the direction SX (i.e. $\phi 1=0°$), substantially parallel to the direction SY (i.e. $\phi1=90°$), or the angle $\phi1$ may be different from $0°$ and different from $90°$.

Figure 10F:
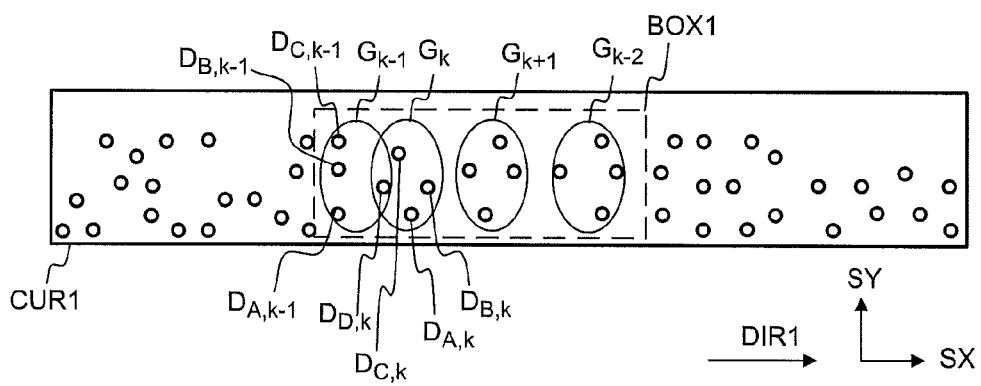
FIG. 10f shows, by way of example, in a side view, a search portion, which contains several sub-patterns.

Referring to FIG. 10f, the monitoring unit 400 may be arranged to determine the distance $L_k$ by using a first sub-pattern $G_k$, which partially overlaps a second sub-pattern $G_{k-1}$. For example, the first sub-pattern $G_k$ may comprise spots $D_{A,k}$, $D_{D,k}$ such that the first sub-pattern $G_k$ does not comprise the spot $D_{A,k-1}$. The second sub-pattern $G_{k-1}$ may comprise spots $D_{A,k-1}$, $D_{D,k}$ such that the second sub-pattern $G_{k-1}$ does not comprise the spot $D_{A,k}$. In other words, the first sub-pattern $G_k$ and the second sub-pattern $G_{k-1}$ may comprise a common spot $D_{D,k}$. For example, the first sub-pattern $G_k$ may comprise the spots $D_{A,k}$, $D_{B,k}$, $D_{C,k}$, $D_{D,k}$ such that first sub-pattern $G_k$ does not comprise the spots $D_{A,k-1}$, $D_{B,k-1}$, $D_{C,k-1}$. The second sub-pattern $G_{k-1}$ may comprise the spots $D_{A,k-1}$, $D_{B,k-1}$, $D_{C,k-1}$, $D_{D,k}$ such that the second sub-pattern $G_{k-1}$ does not comprise the spots $D_{A,k}$, $D_{B,k}$, $D_{C,k}$. Also in this case, the first sub-pattern $G_k$ cannot be transformed into the second sub-pattern $G_{k-1}$ only by a linear transform operation and a scaling operation.

Figure 10G:
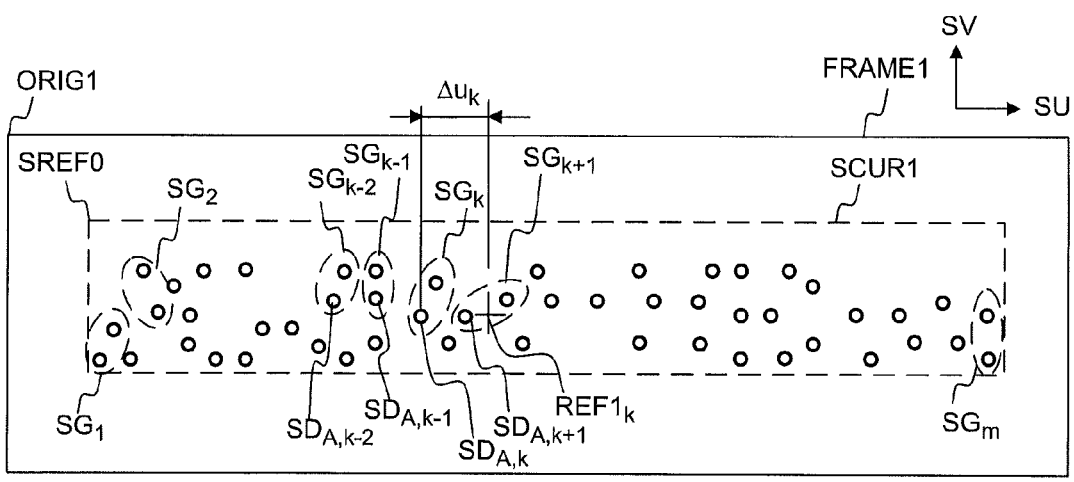
FIG. 10g shows, by way of example, an image of the pattern of FIG. 10a, FIG. 11a shows, by way of example, in a side view, a pointer line projected on the curtain.

Referring to FIG. 10g, an image FRAME1 may comprise one or more sub-images of the pointer features. The image FRAME1 may comprise one or more sub-images $SG_1$, $SG_2$, ..., $SG_{k-2}$, $SG_{k-1}$, $SG_k$, $SG_{k+1}$, ... $SG_m$ of the sub-patterns $G_1$, $G_2$, ..., $G_{k-2}$, $G_{k-1}$, $G_k$, $G_{k+1}$, ... $G_m$. $SD_{A,k-2}$ denotes the sub-image of the pointer feature $D_{A,k-2}$. The image FRAME1 may comprise one or more sub-images $SD_{A,k-2}$, $SD_{B,k-2}$, $SD_{A,k-1}$, $SD_{B,k-1}$, $SD_{A,k-1}$, $SD_{B,k-1}$, $SD_{A,k}$, $SD_{B,k}$, $SD_{A,k+1}$, $SD_{B,k+1}$ of pointer features $D_{A,k-2}$, $D_{B,k-2}$, $D_{A,k-1}$, $D_{B,k-1}$, $D_{A,k-1}$, $D_{B,k-1}$, $D_{A,k}$, $D_{B,k}$, $D_{A,k+1}$, $D_{B,k+1}$. $SD_{A,k-2}$ may denote the sub-image of the feature $D_{A,k-2}$. $SD_{A,k-1}$ may denote the sub-image of the feature $D_{A,k-1}$. $SD_{A,k}$ may denote the sub-image of the feature $D_{A,k}$. $SD_{A,k+1}$ may denote the sub-image of the feature $D_{A,k+1}$. $\Delta u_k$ may denote the displacement of the sub-image $D_{A,k}$ with respect to the reference position $REF1_k$.

Figure 11A:
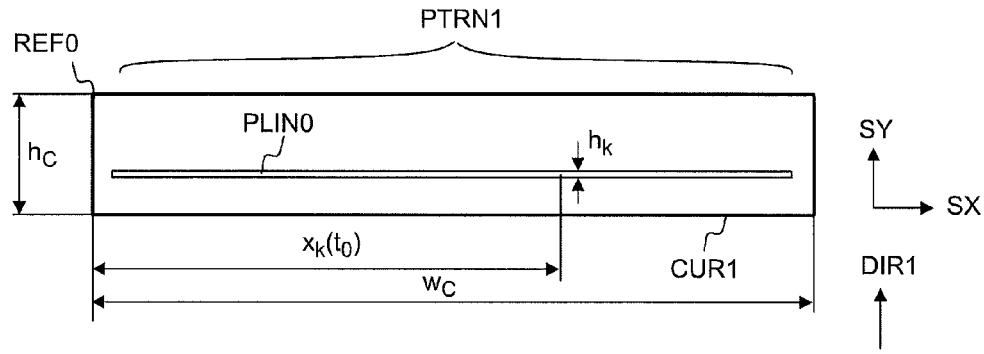
FIG. 11b shows, by way of example, an image of the pointer line in a reference state.
FIG. 11c shows, by way of example, an image of the pointer line in case of a deformed curtain.

Referring to FIG. 11a, the monitoring unit 400 may be arranged to project a pointer line PLIN0 on the curtain CUR1. The projected pattern PTRN1 may be a pointer line PLIN0.

The baseline BL0 of the monitoring unit 400 may be e.g. substantially parallel to the direction SY. The pointer line PLIN0 may have a dimension $h_k$ in the direction SY.

Figure 11B:
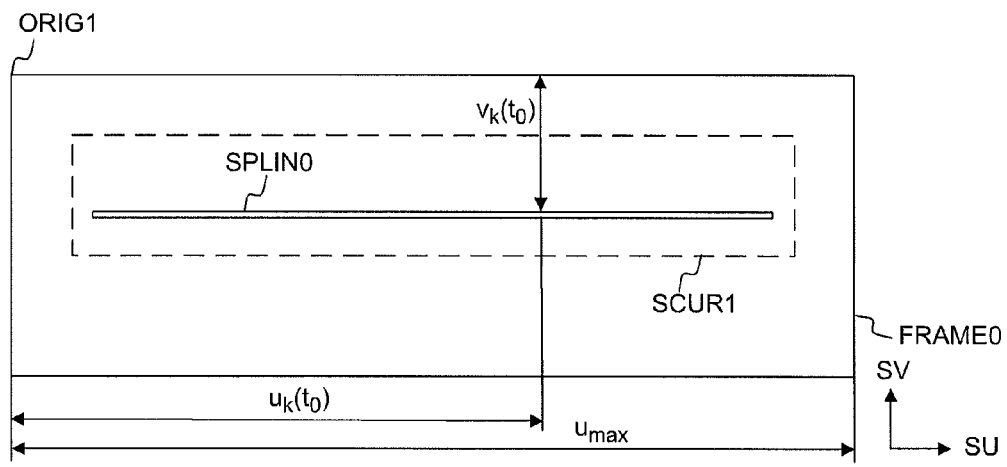

Referring to FIG. 11b, a reference image FRAME0 may comprise a sub-image SPLIN0 of the projected line PLIN0 when the curtain CUR1 is in a reference state.

SU and SV denote orthogonal directions of the image space. The direction SU may correspond to the direction SX of the real space, and the direction SV may correspond to the direction SY of the real space.

Figure 11C:
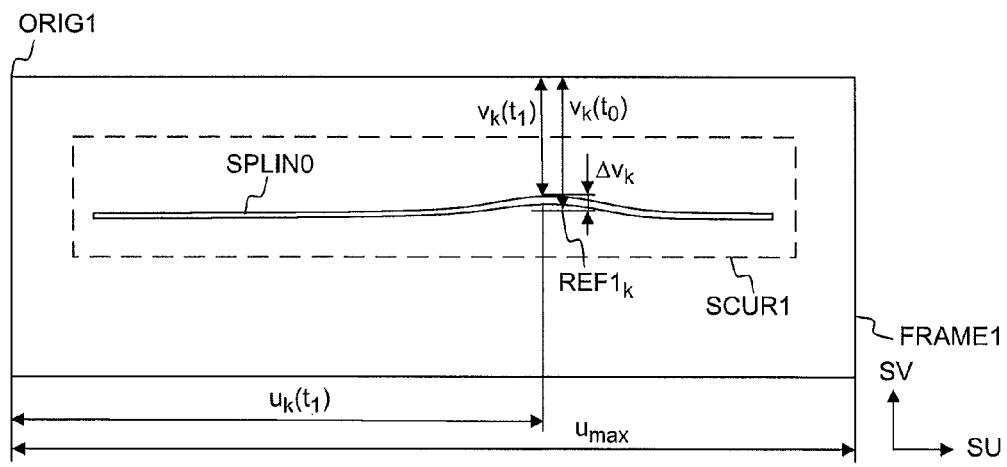

Referring to FIG. 11c, a digital image FRAME1 may comprise a sub-image SPLIN0 of the projected line PLIN0 when the curtain CUR1 is in a deflected and/or deformed state. $\Delta v_k$ may denote a displacement of the sub-image SPLIN0 with respect to a reference position $REF1_k$. Displacement values $\Delta v$ may be determined at several different locations of the sub-image SPLIN0, corresponding to the situation prevailing at a time $t_1$. The displacement values $\Delta v$ may be determined by analyzing the digital image FRAME1. The displacement values $\Delta v$ may be determined by comparing the sub-image SPLIN0 of the digital image FRAME1 with the sub-image SPLIN0 of the reference image FRAME0. Deflection of the curtain CUR1 at several different positions may be determined from the displacement values $\Delta v$ by triangulation.

In particular, the images of the projected line PLIN0 may be captured by using light which is specularly reflected from the front surface FS1 and/or back surface BS1 of the curtain CUR1. In that case the curtain may be very thin and/or it does not need to comprise light-scattering heterogeneous microstructures.

Figure 12:
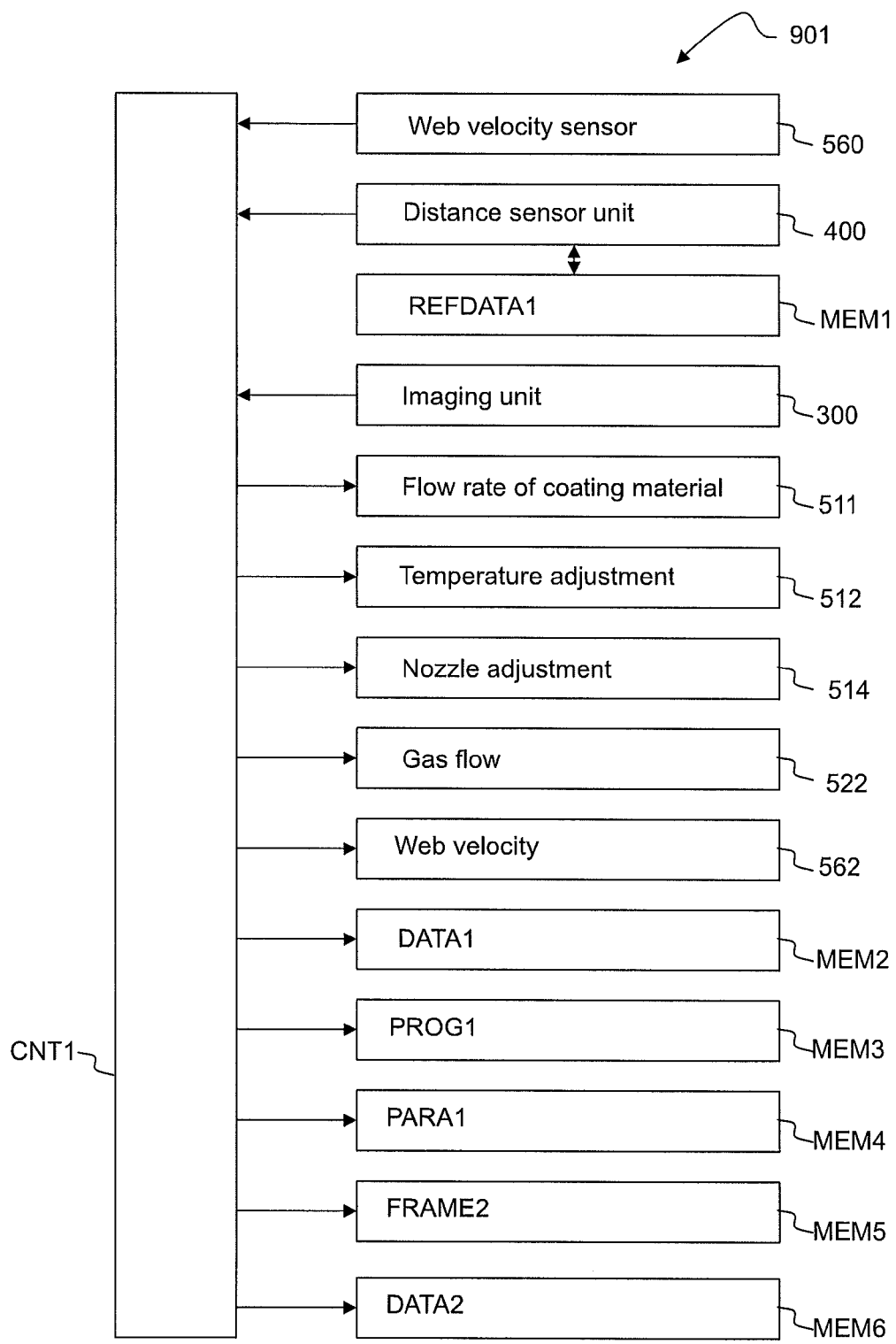
FIG. 12 shows, by way of example, a control system for the curtain coating apparatus.

FIG. 12 shows, by way of example, a data processing system 901 of the curtain coating apparatus 900. The curtain coating apparatus 900 may comprise the data processing system 901. The data processing system 901 may be arranged to e.g. measure data indicative of the state of the curtain CUR1. The data processing system 901 may be arranged to e.g. analyze data provided by the imaging unit 300. The data processing system 901 may be arranged to e.g. process data provided by the monitoring unit 400. The data processing system 901 may be arranged to e.g. control operation of the apparatus 900 based on measured data.

The system 901 may optionally comprise a velocity sensor 560 for measuring the velocity $v_1$ of the primary web WEB0 and/or for measuring the velocity of the coated web WEB1. The velocity sensor 560 may be omitted e.g. when the velocity $v_1$ is known and/or constant.

The system 901 may comprise the monitoring unit 400, which may be arranged to provide position data indicative of the displacement and/or deformation of the material layer monitored by the unit 400.

The system 901 may optionally comprise a memory MEM1 for storing reference data REFDATA1. For example, the memory MEM1 may comprise reference data REFDATA1 for recognizing sub-patterns projected on the curtain. The reference data REFDATA1 may comprise e.g. a reference image FRAME0. The reference data REFDATA1 may comprise coordinates, which define one or more reference positions $REF1_k$.

The system 901 may optionally comprise an imaging unit 300 for capturing digital images of the curtain CUR1. Digital images FRAME2 may be stored e.g. in a memory MEM5. The system 901 may comprise the memory MEM5.

The system 901 may optionally comprise a flow control unit 511 for adjusting/setting the flow rate of coating material ADH0 flowing through a nozzle of the distributing unit 510.

The system 901 may optionally comprise a temperature control unit 512 for controlling temperature of the coating material ADH0 flowing through a nozzle of the distributing unit 510.

The system 901 may optionally comprise an actuator 514 for mechanically adjusting a nozzle of the distributing unit 510. The actuator 514 may be arranged to adjust e.g. an internal dimension of the nozzle, the position of the nozzle and/or the orientation of the nozzle.

The system 901 may optionally comprise a flow control unit 522 for adjusting one or more gas flow rates of the stabilizing unit 520.

The system 901 may optionally comprise a velocity control unit 562 for adjusting, setting and/or controlling the velocity $v_1$ of the web WEB0.

The system 901 may optionally comprise a memory MEM2 for storing data DATA1 indicative of the displacement and/or deformation of the curtain CUR1. The data DATA1 may comprise distance information $(z(t),L_k(t))$. The data DATA1 may comprise shape information. For example, the DATA1 may comprise shape data, which defines the measured shape of the curtain CUR1.

The system 901 may optionally comprise a memory MEM3 for storing computer program code PROG1, which when executed by one or more processors may cause the system 901 to monitor the displacement and/or deformation of the curtain CUR1. The computer program code PROG1 may cause the system 901 to control operation of the apparatus 900 based on the data DATA1.

The system 901 may optionally comprise a memory MEM4 for storing operating parameters PARA1 of the apparatus 900.

The system 901 may optionally comprise a memory MEM5 for storing digital images FRAME2.

The system 901 may optionally comprise a memory MEM6 for storing surveillance data DATA2. The surveillance data DATA2 may e.g. indicate that that a foreign object O1 blocked the view of the monitoring unit 400 during the coating. The surveillance data DATA2 may e.g. indicate a time $t_3$ when the foreign object O1 blocked the view of the monitoring unit 400. The surveillance data DATA2 may e.g. indicate a position $x'_{H,i}, y'_{H,i}$ of an uninspected portion $H_i$ of the coated web WEB1.

The system 901 may comprise a control unit CNT1, which may comprise one or more data processors for monitor the displacement and/or deformation of the curtain CUR1. The system 901 may comprise a control unit CNT1, which may comprise one or more data processors for controlling operation of the apparatus 900 based on the data DATA1.

The monitoring unit 400 may comprise one or more data processors for determining position by triangulation. In an embodiment, one or more data processors may be located in the vicinity of the image sensor 110 of the imaging unit 100. In an embodiment, one or more data processors may be remote from the image sensor 110 of the imaging unit 100.

One or more operating parameters PARA1 of the apparatus 900 may be adjusted based on the distance information provided by the monitoring unit 400. The operating parameters PARA1 may include e.g. the flow rate of the coating material ADH0 via the distributing unit 510, a dimension of a nozzle of the distributing unit 510, the position and/or orientation of the distributing unit 510, a gas flow rate of the stabilizing unit 520. For example, the velocity v1 of the primary web WEB0 may be adjusted based on the distance information provided by the monitoring unit 400. For example, the velocity v1 of the primary web WEB0 may be adjusted substantially to a maximum value where the amplitude of deflection of the curtain CUR1 does not exceed a predetermined limit.

Figure 13:
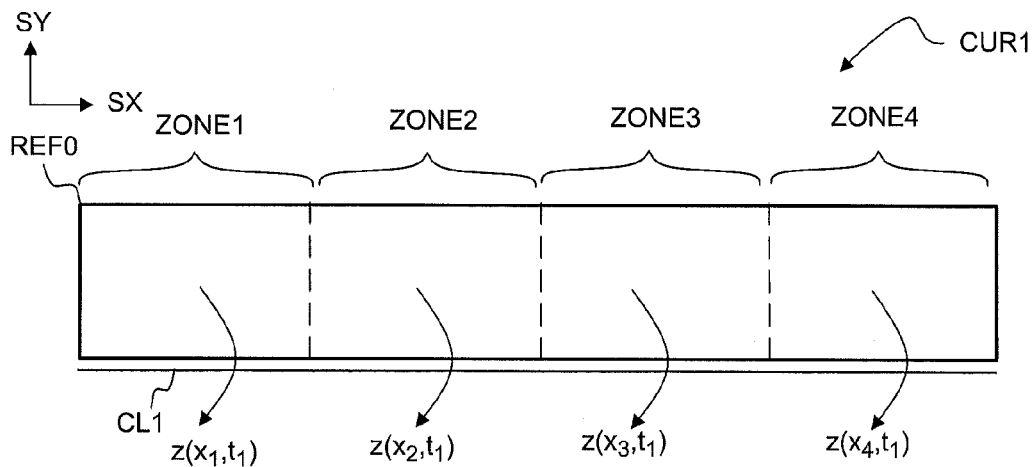
FIG. 13 shows, by way of example, in a side view, providing a spatial distance distribution of the curtain.

Referring to FIG. 13, the curtain CUR1 may be optionally considered to have two or more non-overlapping zones ZONE1, ZONE2, ZONE3, ZONE4. The zones may also be called e.g. as portions. The apparatus 900 may be arranged to measure a position value $z(x_1,t_1)$ indicative of the position of the first zone ZONE1 in the direction SZ at a time $t_1$. The apparatus 900 may be arranged to measure a position value $z(x_2,t_1)$ indicative of the position of the second zone ZONE2 in the direction SZ. The apparatus 900 may be arranged to measure a position value $z(x_3,t_1)$ indicative of the position of the third zone ZONE3 in the direction SZ. The apparatus 900 may be arranged to measure a position value $z(x_4,t_1)$ indicative of the position of the fourth zone ZONE4 in the direction SZ.

The apparatus 900 may be arranged to measure a coordinate value z(t) indicative of the position of each zone. The number of zones may be e.g. in the range of 4 to 20.

The image sensor 110 may comprise a two-dimensional array of detector pixels, wherein the array may have e.g. $N_{HPIX}$ columns. The integer value $N_{HPIX}$ may be e.g. in the range of 200 to 20000. The value $N_{HPIX}$ may be e.g. equal to 640, 800, 1024, 1152, 1280, 1360, 1366, 1400, 1440, 1600, 1680, 1920, 2048, 2560, 3840, 4096, 7680, 8192, or 15360. An image FRAME1 provided by the image sensor 110 may have a resolution according to one or more of the following standards: VGA, SVGA, WSVGA, XGA, WXGA, SXGA, HD, SXGA, WSGA, HD+, UXGA, WSZGA+, FHD, WUXGA, QWXGA, WQHD, WQXGA, 4K, 8KUHD, for example. The number of the zones may be e.g. in the range of 1 to $N_{HPIX}/2$.

Figure 14A:
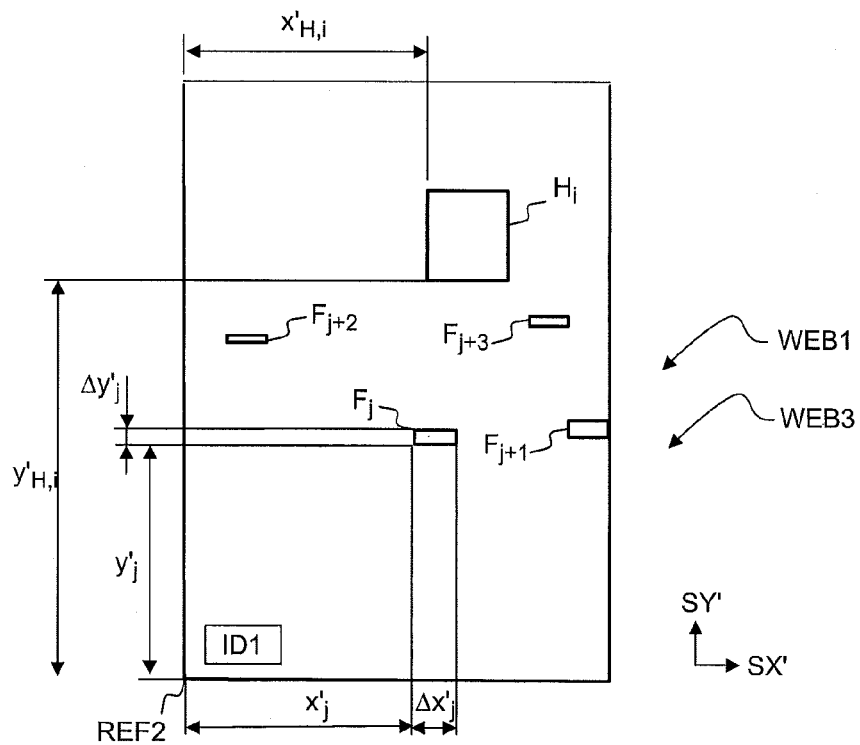
FIG. 14a shows, by way of example, a web having one or more defect portions.

Referring to FIG. 14a, the produced web WEB1, WEB3 may comprise one or more defect portions $F_j$, $F_{j+1}$, $F_{j+2}$, $F_{j+3}$, .... The position of a defect portion $F_j$ may be specified e.g. by providing coordinates $x'_j$, $y'_j$ with respect to a reference point REF2. The defect portion $F_j$ may have a width $\Delta x'_j$ and a height $\Delta y'_j$. The defect portion $F_j$ may be e.g. a portion where the thickness $d_1$ of coating layer ADH1 is lower than a first threshold value. The defect portion $F_j$ may be e.g. a portion where the thickness $d_1$ of the coating layer ADH1 is substantially equal to zero, i.e. the coating layer is missing. The defect portion $F_j$ may be e.g. a portion where the thickness $d_1$ of coating layer ADH1 is higher than a second threshold value. The defect portion $F_j$ may be e.g. a portion where the spatial variations of the thickness $d_1$ of coating layer ADH1 are too high (this may degrade visual appearance of a transparent label).

The shapes of the actual defective areas of the web may deviate from a rectangular form, but the position and size of each defect portion $F_j$, $F_{j+1}$, $F_{j+2}$, $F_{j+3}$ may be defined by a substantially rectangular boundary.

The location of a portion $F_j$ may be associated with a coating time (e.g. $t_1$) when the curtain CUR1 exhibited excessive fluctuations. The locations of the defect portions $F_j$, $F_{j+1}$, $F_{j+2}$, $F_{j+3}$, . . . may be determined e.g. from the distance information provided by the monitoring unit 400. The location of a portion $F_j$ may be associated with a production time $t_1$ when the distance $L_k$ between a pointer feature $D_{A,k}$ and the imaging unit 200 was outside a predetermined range. The apparatus 900 may be configured to provide defect data DATA1, which specifies the locations of the defect portions $F_j$, $F_{j+1}$, $F_{j+2}$, $F_{j+3}$, .... The defect data DATA1 may be provided e.g. by analyzing when the distance $L_k$ between a pointer feature $D_{A,k}$ and the imaging unit 200 was outside a predetermined range.

The location $x'_j,y'_j$ of a defective portion $F_j$ may be associated with a coating time (e.g. $t_2$) when the curtain CUR1 has a void VOID1. The lateral position of the defective portion $F_j$ may correspond to the lateral position of the void VOID1 at the time $t_2$. The defect data DATA1 may be provided e.g. by analyzing when the curtain CUR1 has a void VOID1.

The produced web WEB1, WEB3 may comprise one or more non-inspected portions $H_i$, which were produced when a foreign object partially or completely blocked the field of view VIEW1 of the monitoring unit 400. The locations of the non-inspected portions $H_i$ may be determined e.g. from the distance information provided by the monitoring unit 400. The location $x'_{H,i}, y'_{H,i}$ of a portion $H_i$ may be associated with a coating time (e.g. $t_3$) when the distance $L_k$ between a pointer feature $D_{A,k}$ and the imaging unit 200 was smaller than a predetermined threshold value. In other words, the location $x'_{H,i},y'_{H,i}$ of a portion $H_i$ may be associated with a time $t_3$ when the presence of a foreign object O1 was detected. The location $x'_{H,i},y'_{H,i}$ may be determined by detecting the presence of the foreign object O1.

The presence of a foreign object O1 may be detected based on distance information. The distance information may be provided by detecting the position of a sub-image $(SD_{A,k})$ in an image frame FRAME1B, which may be captured by the image sensor 110 at the time $t_3$.

The apparatus 900 may be configured to provide surveillance data DATA2 indicative of temporary presence of an object O1 during the coating such that the surveillance data DATA2 is associated with one or more portions $H_i$ of the web WEB1, WEB3. The surveillance data DATA2 may be provided e.g. by determining when the distance $L_k$ between a pointer feature $D_{A,k}$ and the imaging unit 200 was smaller than a predetermined threshold value.

The portion $H_i$ may be defective or not defective. The surveillance data DATA2 may merely indicate that information about the quality of the portion $H_i$ is not available, because the presence of the foreign object prevented monitoring the curtain during the time period when the portion $H_i$ was processed. The portion $H_i$ of the web WEB1, WEB3 may be used e.g. for a less demanding application where the quality of the web WEB1, WEB3 is not critical.

The method may comprise:
 forming a curtain of coating material,
 detecting a deformation of the curtain by using an imaging device,
 at least partially blocking a field of view of said imaging device by a foreign object,
 detecting the presence of said foreign object by monitoring a distance between a sensor unit and said object, and
 forming a defect map based on information obtained from the imaging device and based on information about the presence of said foreign object.

The method may comprise:
 forming a curtain of coating material,
 detecting a void in the curtain by using an imaging device,
 at least partially blocking a field of view of said imaging device by a foreign object,
 detecting the presence of said foreign object by monitoring a distance between a sensor unit and said object, and
 forming a defect map based on information obtained from the imaging device and based on information about the presence of said foreign object.

The web WEB1, WEB3 may be associated with an identifier ID1. The identifier ID1 may be e.g. a code, which may be implemented e.g. by using graphical alphanumeric code, a graphical barcode or an RFID tag attached to the WEB1, WEB3 or to a package of the web WEB1, WEB3.

The data DATA1, DATA2 may be associated with the web WEB1, WEB3 e.g. based on the identifier ID1.

The positions $x'_j$, $y'_j$ may be defined e.g. with respect to a reference point REF2. The reference point REF2 may be e.g. a predetermined corner of the web WEB1, WEB3, or a marking produced on the web WEB1, WEB3. The marking may be e.g. a hole, a printed dot or a printed crosshair pattern. The location $x'_{H,i}, y'_{H,i}$ of a portion $H_i$ may be defined e.g. with respect to the reference point REF2.

Figure 14B:
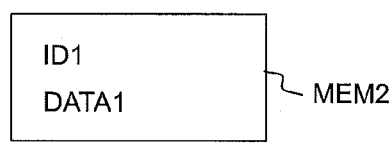
FIG. 14b shows, by way of example, defect data associated with a web

Referring to FIG. 14b, the defect data DATA1 may be stored e.g. in a memory MEM2. The defect data DATA1 may be stored e.g. in a memory of a server, and the defect data DATA1 may be accessed e.g. via the internet. The defect data DATA1 may be associated with the web WEB1, WEB3 e.g. based on an identifier ID1.

Figure 14C:
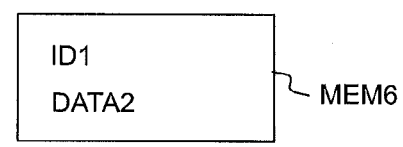
FIG. 14c shows, by way of example, surveillance data associated with a web.

Referring to FIG. 14c, the surveillance data DATA2 may be stored e.g. in a memory MEM6. The surveillance data DATA2 may be stored e.g. in a memory of a server, and the surveillance data DATA2 may be accessed e.g. via the internet. The surveillance data DATA2 may be associated with the web WEB1, WEB3 e.g. based on an identifier ID1.

In an embodiment, the presence of voids VOID1, VOID2 may be detected based on the distance information. The illuminating light beam LB1 may be transmitted through a void VOID1, VOID2 so that the first pointer feature $D_{A,k}$ is projected onto the surface 521 of the stabilizing unit 520. Thus, a void VOID1, VOID2 may be detected by determining whether the distance information $(z(t), L_k(t))$ matches with the position of the surface 521.

In an embodiment, the presence of a single void VOID1, VOID2 may be detected based on pixel value thresholding and based on distance information $(z(t), L_k(t))$. The presence of the void may be detected with very high reliability when the pixel value thresholding indicates the presence of a void, and when the distance information simultaneously indicates the presence of a void at the same location.

The primary web WEB0 and the coated web WEB1 may be moving with respect to the contact line CL1 during the curtain coating. In an embodiment, also the primary web WEB0 may be deflected and/or deformed. In an embodiment, also the coated web WEB1 may be deflected and/or deformed. For example, the primary web WEB0 may be deflected and/or deformed due to a pressure difference caused by the stabilizing unit 520. For example, the coating material ADH0 may comprise a solvent (e.g. water or alcohol), and one or more gas jets may be directed towards the coated web WEB1 in order to accelerate drying of the coated web WEB1. The gas jets may cause deflection and/or deformation of the coated web WEB1. The coated web WEB1 may be wetted by the coating material ADH0 to such a degree that the wetting may cause deflection and/or deformation of the coated web WEB1. The coated web WEB1 may be wetted by the coating material ADH0 to such a degree that one or more holes are formed in the coated web WEB1. In an embodiment, the primary web WEB0 and/or the coated web WEB1 may be supported by an air cushion, which may allow small deflection and/or deformation of the primary web WEB0 and/or the coated web WEB1.

Figure 15:
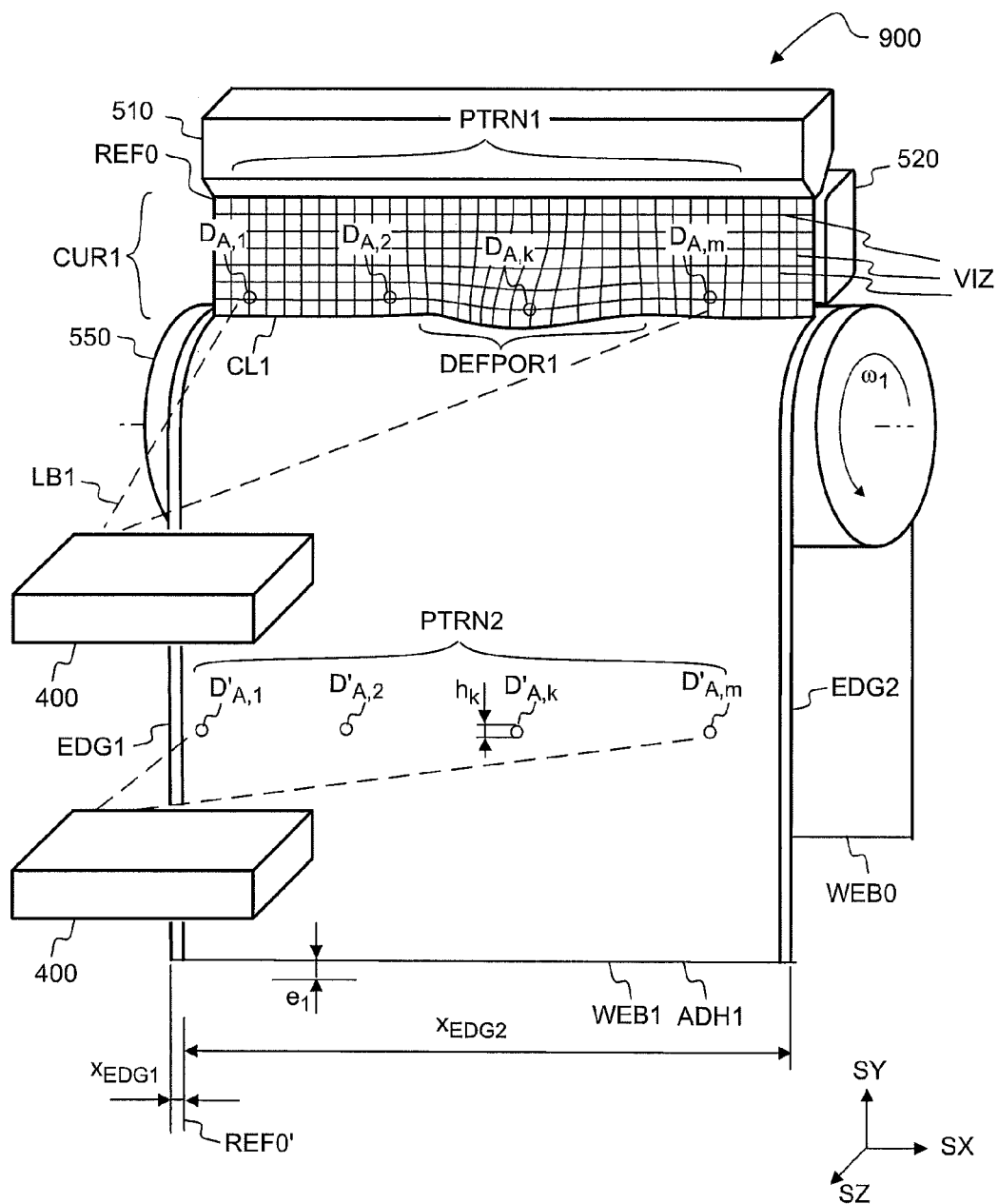
FIG. 15 shows, by way of example, in a three dimensional view, monitoring a moving web during curtain coating.

Referring to FIG. 15, the apparatus 900 may comprise a monitoring unit 400, which may be arranged to monitor deflections, deformations and/or voids of the web WEB0 or WEB1. The distance information may be provided by projecting a primary pattern PTRN2 on primary web WEB0 or on the coated web WEB1. The primary pattern PTRN2 may comprise one or more pointer features $D'_{A,1}$, $D'_{A,2}$, $D'_{A,k}$, $D'_{A,m}$. The primary pattern PTRN2 may comprise a first pointer feature $D'_{A,k}$. The apparatus 900 may be arranged to provide distance information $(z(t), L_k(t))$ by comparing the detected position $(u_k(t_1))$ of the first sub-image $SD'_{A,k}$ of the first pointer feature $D'_{A,k}$ with a reference position $REF1_k$. In an embodiment, the apparatus 900 may comprise a first monitoring unit 400 for projecting a first primary pattern PTRN1 on a first material layer and a second monitoring unit 400 for projecting a second primary pattern PTRN2 on a second material layer.

In an embodiment, the primary pattern PTRN1 may be simultaneously projected on the curtain CUR1 and the on the coated web WEB1. In an embodiment, the primary pattern PTRN1 may be simultaneously projected on the curtain CUR1 and the on the primary web WEB0. In an embodiment, the primary pattern PTRN1 may be projected on the primary web WEB0. In an embodiment, the primary pattern PTRN1 may be projected on the coated web WEB1. A monitoring unit 400 may be arranged to detect whether the moving web WEB0, WEB1 has one or more holes. The monitoring unit 400 may be arranged to detect holes e.g. by pixel value thresholding from a digital image of the web WEB0, WEB1.

A monitoring unit 400 may be arranged to monitor deflections, deformations and/or voids of a moving web WEB0, WEB1, WEB2, or WEB3 during producing a label web WEB1 or a label laminate web WEB3.

The velocity of the web monitored by the unit 400 may be e.g. in the range of 0.5 m/s to 5 m/s. The first image FRAME1 may be captured by using the imaging optics 120, and the distance $L_{NORM}$ between the imaging optics 120 and the primary pattern PTRN1 projected on the web may be e.g. in the range of 1.0 m to 4.0 m. The ratio of the width of the web to the distance $L_{NORM}$ between the imaging optics 120 and the primary pattern PTRN1 may be e.g. in the range of 0.5 to 1.2.

The relatively large distance $L_{NORM}$ may minimize the risk of contaminating the optics with the coating material and/or in order to provide space for maintenance operations. For example, a person O1 may enter to the space between the monitoring unit 400 and the web in order to perform a maintenance operation.

The images of the pointer features may be slightly blurred e.g. due to defocusing, image aberrations and/or motion blurring. The size of the pointer features may be rather large in order to facilitate reliable detection of the pointer features by using the imaging unit 100. For example, the smallest dimension (e.g. height, width or diameter) of the pointer features $D_{A,k}$ may be e.g. greater than 0.001 times the width $w_{WEB}$ of the web monitored by the unit 400. For example, the smallest dimension (e.g. height, width or diameter) of the pointer features $D_{A,k}$ may be e.g. greater than 5 times the thickness of the web monitored by the unit 400.

In an embodiment, the image FRAME1 captured by the imaging unit 100 does not need to reproduce surface roughness of the web. The web may move a distance $e_1$ during the optical exposure time period of the image FRAME1. The pointer feature $D_{A,k}$ may have a height $h_k$ in the direction of movement of the web. In an embodiment, the distance $e_1$ travelled by the web during the optical exposure time period may be e.g. greater than or equal to 50% of the height $h_k$. In an embodiment, the distance $e_1$ travelled by the web during the optical exposure time period may be e.g. greater than or equal to the thickness of the web monitored by the unit 400.

The web has edges EDG1, EDG2. The edges EDG1, EDG2 may be substantially aligned with the direction of movement of the web. The stationaly location reference REF0' may have the same x-coordinate as the location reference REF0. The location reference REF0 may be used as the location reference REF0'.

A monitoring unit 400 may be arranged to monitor instantanous lateral position $x_{EDG1}$, $x_{EDG2}$ of an edge EDG1, EDG2 of the web. The monitoring unit 400 may be arranged to monitor alignment, shrinkage and/or expansion of the web, by using information about the instantanous lateral position $x_{EDG1}$, $x_{EDG2}$ of an edge EDG1, EDG2 of the web. For example, a coating or laminating apparatus may be controlled based on information about the instantanous lateral position of the edge.

In an embodiment, the instantanous lateral position $x_{EDG1}$, $x_{EDG2}$ of an edge EDG1, EDG2 may be monitored with a high reliability by a using the combination of pixel value thresholding and distance information. The instantanous lateral position $x_{EDG1}$, $x_{EDG2}$ of an edge EDG1, EDG2 may be monitored by:
  illuminating the web WEB0, WEB1 with illuminating light LB3,
  capturing a second image FRAME2 of the illuminated web WEB0, WEB1, and
  detecting the position $X_{EDG1}$, $X_{EDG2}$ of an edge EDG1, EDG2 of the web WEB0, WEB1 with respect to a location reference REF0" by using the distance information $(z(t),L_k(t))$ and also by using second information, wherein the second information is obtained by comparing at least one pixel value of the second image FRAME2 with a reference value.

Reliable detection of the edge may be useful e.g. when the web is transparent or translucent.

The method for detecting the position of the edge may comprise simultaneously providing a first light beam $LB1_k$ for projecting a first pointer feature $D_{A,k}$, and providing a second light beam $LB1_{k+1}$ for projecting a second pointer feature $D_{A,k+1}$, wherein an edge EDG1 of the web WEB0, WEB1 may be located such that the web WEB0, WEB1 intersects the first light beam $LB1_k$ but does not intersect the second light beam $LB1_{k+1}$.

In an embodiment, one or more pointer features $D_{A,k}$ of the primary pattern PTRN1 may be projected on a material layer CUR1, WEB0, WEB1, WEB2, WEB3 such that the intensity of the illuminating light LB1 at the position of the pointer feature $D_{A,k}$ is lower than the intensity of the illuminating light LB1 impinging on a region, which surrounds the pointer feature $D_{A,k}$. For example, one or more pointer features $D_{A,k}$ may be dark spots.

Various aspects of the invention are illustrated by the following examples:

Example 1

A method, comprising:
  forming a curtain (CUR1), which comprises a coating material (ADH0),
  forming a coated web (WEB1) by coating a moving primary web (WEB0) with the coating material (ADH0), wherein the curtain (CUR1) and the primary web (WEB1) meet at a contact line (CL1),
  projecting a primary pattern (PTRN1) on a material layer (CUR1, WEB0, WEB1), whose material moves with respect to the contact line (CL1), wherein the primary pattern (PTRN1) comprises a first pointer feature $(D_{A,k})$,
  capturing a first image (FRAME1), which comprises a first sub-image $(SD_{A,k})$ of the first pointer feature $(D_{A,k})$,
  detecting the position $(u_k(t_1))$ of the first sub-image $(SD_{A,k})$ in the first image (FRAME1), and
  providing distance information $(z(t),L_k(t))$ by comparing the detected position $(u_k(t_1))$ of the first sub-image $(SD_{A,k})$ with a reference position $(REF1_k)$.

Example 2

The method of example 1, wherein the primary pattern (PTRN1) is projected on the curtain (CUR1).

Example 3

The method of example 1 or 2 wherein the first pointer feature $(D_{A,k})$ is projected by providing an illuminating light beam $(LB1_k)$, which impinges on the material layer (CUR1), the first image (FRAME1) is captured by focusing light $(LB2_k)$ reflected from the material layer (CUR1), the reflected light (LB2) is focused by imaging optics (120), the first pointer feature $(D_{A,k})$ and a principal point (PP1) of the imaging optics (120) define a line of sight $(VLIN_k)$, an angle $(\gamma_k)$ between the direction of the illuminating light beam $(LB1_k)$ and the line of sight $(VLIN_k)$ is greater than or equal to 0.2 degrees, and the distance information $(z(t),L_k(t))$ is

Example 4

The method according to any of the examples 1 to 3 comprising:
- simultaneously projecting a plurality of pointer features ($D_{A,k-2}$, $D_{A,k-1}$, $D_{A,k}$, $D_{A,k+1}$) on the material layer (CUR1),
- capturing a first image (FRAME1), which comprises sub-images ($SD_{A,k-2}$, $SD_{A,k-1}$, $SD_{A,k}$, $SD_{A,k+1}$) of the pointer features ($D_{A,k-2}$, $D_{A,k-1}$, $D_{A,k}$, $D_{A,k+1}$),
- detecting the positions of the sub-images ($SD_{A,k-2}$, $SD_{A,k-1}$, $SD_{A,k}$, $SD_{A,k+1}$) in the first image (FRAME1), and
- determining distance information ($z(t),L_k(t)$) for several different positions (x), which correspond to the positions of the positions of the pointer features ($D_{A,k-2}$, $D_{A,k-1}$, $D_{A,k}$, $D_{A,k+1}$), wherein the distance information ($z(t),L_k(t)$) is determined from the detected positions of the sub-images ($SD_{A,k-2}$, $SD_{A,k-1}$, $SD_{A,k}$, $SD_{A,k+1}$).

Example 5

The method of example 4, comprising simultaneously projecting a first sub-pattern ($G_k$) and a second sub-pattern ($G_{k+1}$) on the material layer (CUR1), wherein the shapes of the first sub-pattern ($G_k$) and the second sub-pattern ($G_{k+1}$) have been selected such that the first sub-pattern ($G_k$) cannot be transformed into the second sub-pattern ($G_k$) by using only a linear translation operation and a scaling operation.

Example 6

The method according to any of the examples 1 to 3 wherein the primary pattern (PTRN1) is a projected line (PLIN0), wherein a section of the projected line (PLIN0) is used as the first pointer feature ($D_{A,k}$).

Example 7

The method according to any of the examples 1 to 6, comprising forming one or more illuminating light beams ($LB1_k$) by a holographic element (220), and directing the illuminating light beams ($LB1_k$) to the material layer (CUR1) so as to form the primary pattern (PTRN1).

Example 8

The method according to any of the examples 1 to 7 comprising adjusting one or more operating parameters (PARA1) of said coating based on the distance information ($z(t),L_k(t)$).

Example 9

The method according to any of the examples 1 to 8 comprising:
- illuminating the curtain (CUR1) by illuminating light (LB3),
- capturing a second image (FRAME2), which comprises a sub-image (SCUR1) of the curtain (CUR1), and
- detecting a void (VOID1) of the curtain (CUR1) by comparing at least one pixel value of the second image (FRAME2) with a reference value.

Example 10

The method according to any of the examples 1 to 9 comprising producing a label web (WEB1) or a label laminate web (WEB3).

Example 11

The method according to any of the examples 1 to 10 comprising determining defect data (DATA1) by monitoring the curtain (CUR1), wherein the defect data (DATA1) indicates the positions ($x'_j,y'_j$) of one or more defect portions ($F_j$, $F_{j+1}$) of the coated web (WEB1).

Example 12

The method of example 11, comprising die-cutting the web (WEB1, WEB3) according to the defect data (DATA1).

Example 13

The method according to any of the examples 1 to 12, comprising:
- capturing a documentation image (FRAME2) of the curtain (CUR1), and
- storing the documentation image (FRAME2) of the curtain (CUR1) in a memory (MEM5) such that the documentation image (FRAME2) is associated with one or more defect portions ($F_j$) in the coated web (WEB1).

Example 14

The method according to any of the examples 1 to 13, comprising:
- positioning an object (O1) in front of the curtain (CUR1) such that a pointer feature ($D_{A,k}$) is projected on the object (O1),
- capturing a second image (FRAME1B) by using imaging optics (120) such that the second image comprises a sub-image ($SD_{A,k}$) of the pointer feature ($D_{A,k}$) in the second image (FRAME1B), and
- providing surveillance data (DATA2) by detecting the position ($u_k(t_1)$) of the sub-image ($SD_{A,k}$) of the pointer feature ($D_{A,k}$) in the second image (FRAME1B).

Example 15

The method of example 14 comprising providing surveillance data (DATA2) indicative of temporary presence of an object (O1) during the coating such that the surveillance data (DATA2) is associated with one or more portions ($H_i$) of the coated web (WEB1).

Example 16

An apparatus (900), comprising:
- one or more rolls (550) arranged to move a primary web (WEB0),
- a distributor unit (510) arranged to form a curtain (CUR1), which comprises a coating material (ADH0), and to form a coated web (WEB1) by coating the primary web (WEB0) with the coating material (ADH0) such that the curtain (CUR1) meets the primary web (WEB0) at a contact line (CL1),
- a projection unit (200) arranged to project a primary pattern (PTRN1) on a material layer (ADH0, WEB0, WEB1), whose material is arranged to move with respect to the contact line (CL1), wherein the primary pattern (PTRN1) comprises a first pointer feature ($D_{A,k}$), an imaging unit (100) arranged to capture a first image (FRAME1), which comprises a first sub-image ($SD_{A,k}$) of the first pointer feature ($D_{A,k}$), and one or more data processors (CNT1) configured to provide distance information ($z(t), L_k(t)$) by comparing the position ($u_k(t_1)$) of the first sub-image ($SD_{A,k}$) with a reference position ($REF1_k$).

Example 17

The apparatus (900) of example 16 wherein the projection unit (200) is arranged to project the primary pattern (PTRN1) on the curtain (CUR1).

Example 18

The apparatus (900) of example 16 or 17 wherein the distance information is provided by triangulation from the detected position ($u_k(t_1)$) of the first sub-image ($SD_{A,k}$).

Example 19

The apparatus (900) according to any of the examples 16 to 18 wherein the primary pattern (PTRN1) comprises a plurality of distinct pointer features ($D_{A,k-2}$, $D_{A,k-1}$, $D_{A,k}$, $D_{A,k+1}$).

Example 20

The apparatus (900) according to any of the examples 16 to 19 wherein the primary pattern (PTRN1) comprises a first sub-pattern ($G_k$) and a second sub-pattern ($G_{k+1}$) wherein the shapes of the first sub-pattern ($G_k$) and the second sub-pattern ($G_{k+1}$) have been selected such that the first sub-pattern ($G_k$) cannot be transformed into the second sub-pattern ($G_k$) by using only a linear translation operation and a scaling operation.

Example 21

The apparatus (900) according to any of the examples 16 to 18 wherein the primary pattern (PTRN1) is a projected line (PLIN0).

Example 22

The apparatus (900) according to any of the examples 16 to 21 wherein the primary pattern (PTRN1) is projected by using a holographic optical element (220).

Example 23

The apparatus (900) according to any of the examples 16 to 22 wherein the operation of the apparatus (900) is controlled based on the distance information ($z(t), L_k(t)$).

Example 24

The apparatus (900) according to any of the examples 16 to 23 comprising
a light source (600) arranged to provide illuminating light (LB3), and an imaging unit (300) arranged to capture a second image (FRAME2, SCUR1) of the curtain (CUR1), and one or more processors (CNT1) configured to detect a void (VOID1) of the curtain (CUR1) by comparing at least one pixel value of the second image (FRAME2) with a reference value.

Example 25

The apparatus (900) according to any of the examples 16 to 24, wherein the apparatus (900) is arranged to produce a label web (WEB1) or a label laminate web (WEB3).

Example 26

The apparatus (900) according to any of the examples 16 to 25, comprising one or more processors (CNT1) configured to determine defect data (DATA1) by monitoring the curtain (CUR1), wherein the defect data (DATA1) indicates the positions ($x'_j, y'_j$) of one or more defect portions ($F_j$, $F_{j+1}$) of the coated web (WEB1).

Example 27

The apparatus (900) according to any of the examples 16 to 26, comprising:
an imaging unit (300) arranged to capture a documentation image (FRAME2) of the curtain (CUR1), and
a memory (MEM5) for storing the documentation image (FRAME2) of the curtain (CUR1) such that the documentation image (FRAME2) is associated with one or more defect portions ($F_j$) in the coated web (WEB1).

Example 28

The apparatus (900) according to any of the examples 16 to 27, wherein an object can be positioned between the curtain (CUR1) and the imaging unit (100) such that a pointer feature ($D_{A,k}$) is projected on the object (O1), wherein the imaging unit (100) is arranged to capture a second image (FRAME1B) such that the second image comprises a sub-image ($SD_{A,k}$) of the pointer feature ($D_{A,k}$), and one or more processors are arranged to provide surveillance data (DATA2) by detecting the position ($u_k(t_1)$) of the sub-image ($SD_{A,k}$) of the pointer feature ($D_{A,k}$) in the second image (FRAME1B).

Example 29

An apparatus (900), configured to:
form a curtain (CUR1), which comprises a coating material (ADH0),
form a coated web (WEB1) by coating a moving primary web (WEB0) with the coating material (ADH0),
project a primary pattern (PTRN1) on the curtain (CUR1), wherein the primary pattern (PTRN1) comprises a first pointer feature ($D_{A,k}$),
capture a first image (FRAME1), which comprises a first sub-image ($SD_{A,k}$) of the first pointer feature ($D_{A,k}$),
detect the position ($u_k(t_1)$) of the first sub-image ($SD_{A,k}$) in the first image (FRAME1), and
provide distance information ($z(t), L_k(t)$) by comparing the detected position ($u_k(t_1)$) of the first sub-image ($SD_{A,k}$) with a reference position ($REF1_k$).

Example 30

A computer program (PROG1) comprising computer program code configured to, when executed on at least one processor (CNT1), cause an apparatus or a system to:

form a curtain (CUR1), which comprises a coating material (ADH0),
form a coated web (WEB1) by coating a moving primary web (WEB0) with the coating material (ADH0),
project a primary pattern (PTRN1) on the curtain (CUR1), wherein the primary pattern (PTRN1) comprises a first pointer feature ($D_{A,k}$),
capture a first image (FRAME1), which comprises a first sub-image ($SD_{A,k}$) of the first pointer feature ($D_{A,k}$),
detect the position ($u_k(t_1)$) of the first sub-image ($SD_{A,k}$) in the first image (FRAME1), and
provide distance information ($z(t),L_k(t)$) by comparing the detected position ($u_k(t_1)$) of the first sub-image ($SD_{A,k}$) with a reference position ($REF1_k$).

Example 31

A computer program product embodied on a non-transitory computer readable medium (MEM3), comprising computer program code (PROG1) configured to, when executed on at least one processor, cause an apparatus or a system to:
form a curtain (CUR1), which comprises a coating material (ADH0),
form a coated web (WEB1) by coating a moving primary web (WEB0) with the coating material (ADH0),
project a primary pattern (PTRN1) on the curtain (CUR1), wherein the primary pattern (PTRN1) comprises a first pointer feature ($D_{A,k}$),
capture a first image (FRAME1), which comprises a first sub-image ($SD_{A,k}$) of the first pointer feature ($D_{A,k}$),
detect the position ($u_k(t_1)$) of the first sub-image ($SD_{A,k}$) in the first image (FRAME1), and
provide distance information ($z(t),L_k(t)$) by comparing the detected position ($u_k(t_1)$) of the first sub-image ($SD_{A,k}$) with a reference position ($REF1_k$).

Example 32

A combination of a web (WEB1, WEB3) and data (DATA1), wherein the web (WEB1, WEB3) has been produced by curtain coating, and the data (DATA1) comprises defect data, which indicates the positions ($x'_j,y'_j$) of one or more defect portions ($F_j$, $F_{j+1}$) of the web (WEB1,WEB3).

Example 33

The combination of example 32 wherein the data (DATA1) further comprises surveillance data (DATA2) indicative of temporary presence of an object (O1) during the curtain coating, wherein the surveillance data (DATA2) is associated with one or more portions of the web (WEB1, WEB3).

34. A method, comprising:
projecting a primary pattern (PTRN1) on a moving web (WEB0, WEB1), wherein the primary pattern (PTRN1) comprises a plurality of pointer features ($D_{A,k-2}$, $D_{A,k-1}$, $D_{A,k}$, $D_{A,k+1}$),
capturing a first image (FRAME1), which comprises sub-images ($SD_{A,k-2}$, $SD_{A,k}$, $SD_{A,k+1}$) of the pointer features ($D_{A,k-2}$, $D_{A,k-1}$, $D_{A,k}$, $D_{A,k+1}$),
detecting the positions of the sub-images ($SD_{A,k-2}$, $SD_{A,k}$, $SD_{A,k+1}$), and
providing distance information ($z(t),L_k(t)$) by comparing the detected position ($u_k(t_1)$) of a first sub-image ($SD_{A,k}$) with a reference position ($REF1_k$) of said first sub-image ($SD_{A,k}$).

Example 35

The method of example 34 comprising measuring deflection and/or deformation of the web (WEB0, WEB1) based on the detected positions of the sub-images ($SD_{A,k-2}$, $SD_{A,k-1}$, $SD_{A,k}$, $SD_{A,k+1}$).

Example 36

The method of example 34 or 35 comprising:
illuminating the web (WEB0, WEB1) with illuminating light (LB3),
capturing a second image (FRAME2) of the illuminated web (WEB0, WEB1), and
detecting a void (VOID1) of the web (WEB0, WEB1) by using the distance information ($z(t),L_k(t)$) and also by using second information, wherein the second information is obtained by comparing at least one pixel value of the second image (FRAME2) with a reference value.

Example 37

The method of example 34 or 35 comprising:
illuminating the web (WEB0, WEB1) with illuminating light (LB3),
capturing a second image (FRAME2) of the illuminated web (WEB0, WEB1), and
detecting the position ($x_{EDG1}$, $x_{EDG2}$) of an edge (EDG1, EDG2) of the web (WEB0, WEB1) with respect to a location reference (REF0') by using the distance information ($z(t),L_k(t)$) and also by using second information, wherein the second information is obtained by comparing at least one pixel value of the second image (FRAME2) with a reference value.

Example 38

The method of example 37 comprising simultaneously providing a first light beam ($LB1_k$) for projecting a first pointer feature ($D_{A,k}$), and providing a second light beam ($LB1_{k+i}$) for projecting a second pointer feature ($D_{A,k+1}$), wherein an edge (EDG1) of the web (WEB0, WEB1) is located such that the web (WEB0, WEB1) intersects the first light beam ($LB1_k$) but does not intersect the second light beam ($LB1_{k+1}$).

Example 39

The method according to any of the examples 34 to 38, comprising simultaneously projecting a first sub-pattern ($G_k$) and a second sub-pattern ($G_{k+1}$) on the web (WEB0, WEB1), wherein the shapes of the first sub-pattern ($G_k$) and the second sub-pattern ($G_{k+1}$) have been selected such that the first sub-pattern ($G_k$) cannot be transformed into the second sub-pattern ($G_k$) by using only a linear translation operation and a scaling operation.

Example 40

The method according to any of the examples 34 to 39 comprising forming one or more illuminating light beams ($LB1_k$) by a holographic element (220), and directing the illuminating light beams ($LB1_k$) to the material layer (CUR1) so as to form the primary pattern (PTRN1).

Example 41

The method according to any of the examples 34 to 40 wherein the velocity (v1) of the web (WEB0, WEB1) is in the range of 0.5 m/s to 5 m/s.

Example 42

The method according to any of the examples 34 to 41 wherein the first image is captured by using imaging optics (120), and the distance ($L_{NORM}$) between the imaging optics (120) and the primary pattern (PTRN1) projected on the web (WEB0, WEB1) is in the range of 1.0 m to 4.0 m.

Example 43

The method according to any of the examples 34 to 42 wherein the ratio of the width ($w_{WEB}$) of the web (WEB0, WEB1) to the distance ($L_{NORM}$) between the imaging optics (120) and the primary pattern (PTRN1) is in the range of 0.5 to 1.2.

Example 44

The method according to any of the examples 34 to 43 wherein the thickness of the web (WEB0, WEB1) is in the range of 0.01 mm to 0.5 mm, in particular in the range of 0.02 mm to 0.3 mm.

Example 45

The method according to any of the examples 34 to 44 wherein the web (WEB0, WEB1) is transparent or translucent.

Example 46

The method according to any of the examples 34 to 45 wherein the web (WEB0, WEB1) comprises paper and/or plastic, in particular polyester and/or polypropylene.

Example 47

The method according to any of the examples 34 to 46 wherein the web (WEB0, WEB1) comprises an adhesive layer and/or an anti adhesion layer.

For the person skilled in the art, it will be clear that modifications and variations of the devices and the methods according to the present invention are perceivable. The figures are schematic. The particular embodiments described above with reference to the accompanying drawings are illustrative only and not meant to limit the scope of the invention, which is defined by the appended claims.

What is claimed is:

1. A method, comprising:
    forming a curtain comprising a coating material;
    forming a coated web by coating a moving primary web with the coating material, wherein the curtain and the primary web meet at a contact line;
    projecting a primary pattern on the curtain, wherein the primary pattern comprises a first pointer feature;
    capturing a first image comprising a first sub-image of the first pointer feature;
    detecting the position of the first sub-image in the first image;
    providing distance information by comparing the detected position of the first sub-image with a reference position;
    detecting a temporary presence of an object in front of the curtain; and
    providing surveillance data indicative of the temporary presence of the object during the coating such that the surveillance data is associated with at least one portion of the coated web.

2. The method according to claim 1, wherein the primary pattern is projected on the curtain.

3. The method according to claim 1, wherein the first pointer feature is projected by providing an illuminating light beam that impinges on the curtain, the first image is capture by focusing light reflected from the curtain, the reflected light is focused by imaging optics, the first pointer feature and a principal point of the imaging optics define a line of sight, an angle between the direction of the illuminating light beam and the line of sight is greater than or equal to 0.2 degrees, and the distance information is determined by triangulation from the detected position of the first sub-image.

4. The method according to claim 1, further comprising:
    simultaneously projecting a plurality of pointer features on the curtain;
    capturing the first image, which comprises sub-images of the plurality of pointer features;
    detecting the positions of the sub-images in the first image; and
    determining distance information for several different positions, wherein the distance information is determined from the detected positions of the sub-images.

5. The method according to claim 1, further comprising:
    simultaneously projecting a first sub-pattern and a second sub-pattern on the curtain, wherein the shapes of the first sub-pattern and the second sub-pattern have been selected such that the first sub-pattern cannot be transformed into the second sub-pattern by using only a linear translation operation and a scaling operation.

6. The method according to claim 1, wherein the primary pattern is a projected line, and wherein a section of the projected line is used as the first pointer feature.

7. The method according to claim 1, further comprising:
    forming at least one illuminating light beam by a holographic element; and
    directing the illuminating light beams to the curtain so as to form the primary pattern.

8. The method according to claim 1, further comprising:
    adjusting at least one operating parameter of said coating based on the distance information.

9. The method according to claim 1, further comprising:
    illuminating the curtain by illuminating light;
    capturing a second image, which comprises a sub-image of the curtain; and
    detecting a void of the curtain by comparing at least one pixel value of the second image with a reference value.

10. The method according to claim 1, further comprising:
    producing a label web or a label laminate web.

11. The method according to claim 1, further comprising:
    determining defect data by monitoring the curtain, wherein the defect data indicates the positions of at least one defect portion of the coated web.

12. The method according to claim 11, further comprising:
    die-cutting the web according to the defect data.

13. The method according to claim 1, further comprising:
capturing a documentation image of the curtain; and
storing the documentation image of the curtain in a memory such that the documentation image is associated with one or more defect portions in the coated web.

14. The method according to claim 1, further comprising:
positioning an object in front of the curtain such that the first pointer feature is temporarily projected on the object;
capturing a second image by using imaging optics such that the second image comprises a sub-image of the first pointer feature in the second image, and
providing surveillance data by detecting the position of the sub-image of the first pointer feature in the second image.

* * * * *